United States Patent [19]
Itoh et al.

[11] Patent Number: 5,545,652
[45] Date of Patent: Aug. 13, 1996

[54] TRIAZOLE AND IMIDAZOLE COMPOUNDS AND THEIR USE AS ANTIFUNGAL THERAPEUTIC AGENTS

[75] Inventors: Katsumi Itoh, Toyono-gun; Kenji Okonogi, Mishima-gun; Akihiro Tasaka, Suita, all of Japan

[73] Assignee: Takeda Chemical Industries, Ltd., Osaka, Japan

[21] Appl. No.: 310,995

[22] Filed: Sep. 23, 1994

[30] Foreign Application Priority Data

Sep. 24, 1993 [JP] Japan .................................. 5-238340
Aug. 12, 1994 [JP] Japan .................................. 6-190766

[51] Int. Cl.$^6$ .................. A61K 31/41; A61K 31/415; C07D 249/08; C07D 403/10

[52] U.S. Cl. .................. 514/383; 514/252; 514/397; 544/366; 548/267.8; 548/313.7

[58] Field of Search .................. 548/267.8, 313.7, 548/314.7; 546/210; 544/370, 366; 514/383

[56] References Cited

U.S. PATENT DOCUMENTS

| | | | |
|---|---|---|---|
| 4,753,957 | 6/1988 | Chan | 514/391 |
| 5,371,101 | 12/1994 | Itoh et al. | 514/383 |

FOREIGN PATENT DOCUMENTS

| | | |
|---|---|---|
| 0054974 | 6/1982 | European Pat. Off. . |
| 0122693 | 10/1984 | European Pat. Off. . |
| 0122056 | 10/1984 | European Pat. Off. . |
| 0321131 | 6/1989 | European Pat. Off. . |
| 0332387 | 9/1989 | European Pat. Off. . |
| 0567982 | 11/1993 | European Pat. Off. . |
| 2159148 | 11/1985 | United Kingdom . |

OTHER PUBLICATIONS

Konosu et al., "Triazole Antifungals, IV. Synthesis And Antifungal Activities Of 3-Acylamino-2-aryl-2-butanol Derivatives", *Chem. Pharm. Bull.*, vol. 39(10):2581–2589, Oct. (1991).

*Primary Examiner*—Johann Richter
*Assistant Examiner*—Laura L. Stockton
*Attorney, Agent, or Firm*—Foley & Lardner

[57] ABSTRACT

The present invention provides an azole compound represented by the formula (I):

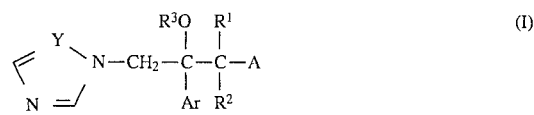

wherein Ar is an optionally-substituted phenyl group; $R^1$ and $R^2$ are, the same or different, a hydrogen atom or a lower alkyl group, or $R^1$ and $R^2$ may combine together to form a lower alkylene group; $R^3$ is a hydrogen atom or an acyl group; Y is a nitrogen atom or a methine group; and A is an optionally-substituted saturated cyclic amide group bonded through a first nitrogen atom, or a salt thereof, which is useful for prevention and therapy of fungal infections of mammals as antifungal agent.

12 Claims, No Drawings

TRIAZOLE AND IMIDAZOLE COMPOUNDS AND THEIR USE AS ANTIFUNGAL THERAPEUTIC AGENTS

DESCRIPTION OF THE PRESENT INVENTION

1. Field of the Invention

The present invention relates to azole compounds which are useful as an antifungal therapeutic agent and a method of manufacturing the same as well as the use thereof.

2. Prior Art

Various azole compounds exhibiting antifungal activity have been reported (for example, EP0122056A1, EP0332387A1 and EP0122693A1).

However, these azole compounds are not satisfactory as pharmaceutical agents in terms of antifungal activity, antifungal spectrum, adverse reaction and the pharmacokinetics.

There has been a demand for the compounds which exhibit higher safety, better absorption in vivo and higher antifungal activity as an antifungal therapeutic agent.

SUMMARY OF THE INVENTION

The present invention relates to:

(1) a compound represented by the formula (I):

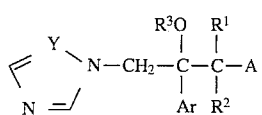

wherein Ar is an optionally-substituted phenyl group; $R^1$ and $R^2$ are, the same or different, a hydrogen atom or a lower alkyl group, or $R^1$ and $R^2$ may combine together to form a lower alkylene group; $R^3$ is a hydrogen atom or an acyl group; Y is a nitrogen atom or a methine group; and A is an optionally-substituted saturated cyclic amide group bonded through a first nitrogen atom, or a salt thereof, (2) a compound described in (1) above in which one of $R^1$ and $R^2$ is a hydrogen atom and another is a lower alkyl group, (3) a compound described in (1) above in which Y is a nitrogen atom, (4) a compound described in (1) above in which Ar is a halogen-substituted phenyl group, (5) a compound described in (4) above in which Ar is a phenyl group substituted with 1 or 2 fluorine atoms, (6) a compound described in (1) above in which A is a five- or six-membered saturated cyclic amide group, (7) a compound described in (1) above in which A is a saturated cyclic amide group having a second nitrogen atom in the ring, (8) a compound described in (7) above in which the second nitrogen atom of the saturated cyclic amide group is attached to a substituent, (9) a compound described in (1) above in which A is a 3-substituted phenyl-2-oxo-1-imidazolidinyl group of the formula:

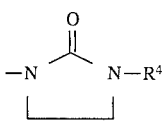

wherein $R^4$ is a substituted phenyl group,

(10) a compound described in (1) above in which A is a 4-substituted phenyl-2,5-dioxo-1-piperazinyl group of the formula:

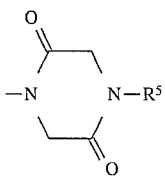

wherein $R^5$ has the same meaning of $R^4$.

(11) a compound described in (1) above in which A is a saturated cyclic amide group substituted with a substituted phenyl group having 1 or 2 substituents selected from the group consisting of a halogen atom, a halogenated $C_{1-6}$ alkyl group and a halogenated $C_{1-6}$ alkoxy group,

(12) a compound described in (11) above in which the substituent of the substituted phenyl group is a fluorine atom, a fluorinated lower alkyl group or a fluorinated lower alkoxy group,

(13) a process for preparing a compound of the formula (I) described in (1) above or a salt thereof which comprises reacting a compound represented by the formula (II):

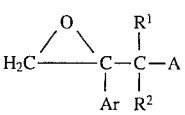

wherein Ar is an optionally-substituted phenyl group; $R^1$, and $R^2$ are, the same or different, a hydrogen atom or a lower alkyl group, or $R^1$ and $R^2$ may combine together to form a lower alkylene group; and A is an optionally-substituted saturated cyclic amide group bonded through a first nitrogen atom, with a compound represented by the formula (III):

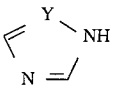

wherein Y is a nitrogen atom or a methine group, or a salt thereof to give a compound of the formula (I) in which $R^3$ is a hydrogen atom, if necessary followed by treating with an acylating agent to obtain a compound of the formula (I) in which $R^3$ is an acyl group,

(14) a process for preparing a compound of the formula (I) described in (9) above or a salt thereof which comprises reducing a compound represented by the formula (I'):

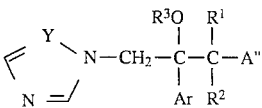

wherein Ar is an optionally-substituted phenyl group; $R^1$ and $R^2$ are, the same or different, a hydrogen atom or a lower alkyl group, or $R^1$ and $R^2$ may combine together to form a lower alkylene group; $R^3$ is a hydrogen atom or an acyl group; Y is a nitrogen atom or a methine group; and A" is a 3-substituted phenyl-2-oxo-2,3-dihydro-1H-imidazol-1-yl group, or a salt thereof, and

(15) an antifungal agent which comprises a compound (I) described in (1) above or a pharmaceutically acceptable salt thereof, excipient and/or carrier.

DETAILED DESCRIPTION OF THE PREFERRED EMBODIMENT

Examples of the substituents for the optionally-substituted phenyl group represented by Ar in the formulae (I), (II) and (I') are a halogen (for example, fluorine, chlorine, bromine or iodine), a halogenated lower $(C_{1-4})$ alkyl group, a halogenated lower $(C_{1-4})$ alkoxy group, a lower $(C_{1-4})$ alkylsulfonyl group and a halogenated lower $(C_{1-4})$ alkylsulfonyl group. Preferably, the substituent is a halogen (for example, fluorine, chlorine, bromine or iodine) and, particularly preferably, it is fluorine. Numbers of the substituents are preferably from 1 to 3 and, more preferably, 1 or 2.

Examples of Ar are a halogenophenyl group, a halogenated lower $(C_{1-4})$ alkylphenyl group, a halogenated lower $(C_{1-4})$ alkoxyphenyl group, a lower $(C_{1-4})$ alkylsulfonylphenyl group and a halogenated lower $(C_{1-4})$ alkylsulfonylphenyl group.

In the above, examples of the halogenophenyl groups are 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl, 2,4,6-trifluorophenyl and 4-bromophenyl.

Examples of the halogenated lower $(C_{1-4})$ alkylphenyl groups are 4-trifluoromethylphenyl group and the like.

Examples of the halogenated lower $(C_{1-4})$ alkoxyphenyl groups are 4-trifluoromethoxyphenyl, 4-(1,1,2,2-tetrafluoroethoxy)phenyl, 4-(2,2,2-trifluoroethoxy)phenyl, 4-(2,2,3,3-tetrafluoropropoxy)phenyl and 4-(2,2,3,3,3-pentafluoropropoxy)phenyl.

Examples of the lower $(C_{1-4})$ alkylsulfonylphenyl groups are 4-methanesulfonylphenyl and the like.

Examples of the halogenated lower $(C_{1-4})$ alkylsulfonylphenyl groups are 4-(2,2,2-trifluoroethanesulfonyl)phenyl, 4-(2,2,3,3-tetrafluoropropanesulfonyl)phenyl and 4-(2,2,3,3,3-pentafluoropropanesulfonyl)phenyl.

Preferred Ar is a phenyl group which is substituted particularly with 1 or 2 halogens such as 2,4-difluorophenyl, 2,4-dichlorophenyl, 4-chlorophenyl, 4-fluorophenyl, 2-chlorophenyl, 2-fluorophenyl, 2-fluoro-4-chlorophenyl, 2-chloro-4-fluorophenyl and 4-bromophenyl and, among which 4-fluorophenyl, 2-fluorophenyl and 2,4-difluorophenyl are especially preferred.

Examples of the lower alkyl groups represented by $R^1$ or $R^2$ in the formulae (I), (II) and (I') are straight chain or branched alkyl groups having 1 to 4 carbon atoms such as methyl, ethyl, propyl, isopropyl, butyl, isobutyl, sec-butyl and tert-butyl and, among which methyl is preferred. Preferred combinations of $R^1$ and $R^2$ are hydrogen and hydrogen; hydrogen and methyl; or methyl and methyl. Examples of the lower alkylene groups formed by connection of $R^1$ and $R^2$ are straight lower $(C_{2-4})$ alkylene groups such as ethylene, propylene and butylene and, among which ethylene is preferred.

Among them, it is preferable that one of $R^1$ and $R^2$ is a hydrogen atom and the other is a methyl group.

Examples of the acyl groups represented by $R^3$ in the formulae (I) and (I') are acyl groups derived from organic carboxylic acids such as an alkanoyl group, preferably that with 1–7 carbon atoms (e.g., formyl, acetyl, propionyl, butyryl, isobutyryl, pentanoyl, hexanoyl or heptanoyl), particularly preferably that with 1–3 carbon atoms; an arylcarbonyl group, preferably that with 7–15 carbon atoms (e.g., benzoyl or naphthalenecarbonyl), particularly preferably that with 7–11 carbon atoms; an alkoxycarbonyl group, preferably that with 2–7 carbon atoms (e.g., methoxycarbonyl, ethoxycarbonyl, propoxycarbonyl, isopropoxycarbonyl, butoxycarbonyl, isobutoxycarbonyl, sec-butoxycarbonyl or tert-butoxycarbonyl), particularly preferably that with 2–4 carbon atoms; an aryloxycarbonyl group, preferably that with 7–15 carbon atoms (e.g., phenoxycarbonyl), particularly preferably that with 7–11 carbon atoms; an aralkylcarbonyl group, preferably that with 8–20 carbon atoms (e.g., benzylcarbonyl, phenethylcarbonyl, phenylpropylcarbonyl or naphthylethylcarbonyl), particularly preferably that with 8–14 carbon atoms. Those may be substituted with suitable one to three substituent(s). Examples of suitable substituents are an optionally-halogenated lower alkyl group, an aryl group and a halogen.

Preferably, the above acyl groups are those which can be hydrolyzed in vivo. Specific examples thereof are formyl, acetyl, benzoyl and benzylcarbonyl.

The saturated cyclic amide group in the optionally-substituted saturated cyclic amide group bonded through a nitrogen atom represented by A in the formulae (I) and (II) is preferably a saturated heterocyclic group which has one to three nitrogen atoms and may have one oxygen or sulfur atom in a ring represented by a formula:

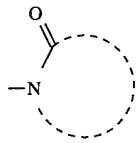

The above-mentioned saturated cyclic amide groups are a four- to eight-membered cyclic groups and, preferably, a five- or six-membered cyclic group. Examples of such saturated cyclic amide groups are 2-oxo-1-imidazolidinyl, 5-oxo-1-imidazolidinyl, 2-oxo-1-pyrrolidinyl, 3-oxo-2-pyrazolidinyl, 2-oxo-1-piperazinyl, 2-oxo-1-piperidinyl, 3-oxomorpholino and 2-oxo-1-perhydropyrimidinyl.

It is particularly preferred that the saturated cyclic amide group has two nitrogen atoms in the ring. Examples of such saturated cyclic amide groups are 2-oxo-1-imidazolidinyl, 2-oxo-1-piperazinyl and 2-oxo-1-perhydropyrimidinyl.

Examples of the substituents in the saturated cyclic amide group represented by A are an oxo group, a halogen (for example, fluorine, chlorine, bromine or iodine), an aliphatic hydrocarbon group which may be substituted, an aromatic hydrocarbon group which may be substituted and an aromatic hetero cyclic group which may be substituted. The number of substituents in the saturated cyclic amide group is 1 to 3, preferably 1 or 2.

In case where the substituents in the saturated cyclic amide group represented by A is the optionally substituted aliphatic hydrocarbon group, examples of the aliphatic hydrocarbon groups are alkyl, cycloalkyl, alkenyl and alkynyl.

Examples of such alkyl groups are straight chain or branched alkyl groups having 1 to 12 carbon atoms such as methyl, ethyl, n-propyl, isopropyl, n-butyl, isobutyl, sec-butyl, tert-butyl, heptyl, octyl, nonyl, decyl and dodecyl, among which lower alkyl groups having 1 to 4 carbon atoms (e.g., methyl, ethyl, n-propyl isopropyl, n-butyl, isobutyl, sec-butyl or tert-butyl) are preferred.

Examples of the cycloalkyl groups are cycloalkyl groups having 3 to 8 carbon atoms such as cyclopropyl, cyclobutyl, cyclopentyl, cyclohexyl, cycloheptyl and cyclooctyl, among which cycloalkyl groups having 3 to 6 carbon atoms (e.g., cyclopropyl, cyclobutyl, cyclopentyl or cyclohexyl) are preferred.

Examples of the alkenyl groups are alkenyl groups having 2 to 4 carbon atoms such as vinyl, propenyl and butenyl, among which alkenyl groups having 2 to 3 carbon atoms (e.g., vinyl or propenyl) are preferred.

Examples of the alkynyl groups are alkynyl groups having 2 to 4 carbon atoms such as ethynyl, propynyl and butynyl, among which alkynyl groups having 2 to 3 carbon atoms (e.g., ethynyl or propynyl) are preferred.

In case where the substituents in the saturated cyclic amide group represented by A is the optionally substituted aromatic hydrocarbon group, examples of the aromatic hydrocarbon groups are aryl groups having 6 to 14 carbon atoms. Examples of the aryl groups are phenyl, naphthyl, biphenylyl, anthryl and indenyl, among which aryl groups having 6 to 10 carbon atoms (e.g., phenyl or naphthyl) are preferred.

In case where the substituents in the saturated cyclic amide group represented by A is the optionally substituted aromatic heterocyclic group, examples of the aromatic heterocyclic groups are aromatic heterocyclic groups having at least one hetero atom selected from a nitrogen atom, a sulfur atom and an oxygen atom. The aromatic heterocyclic groups may be condensed with a benzene ring, five-membered heterocycle or six-membered heterocycle. Examples of the aromatic heterocyclic groups are aromatic heterocyclic groups such as imidazolyl, triazolyl, tetrazolyl, pyrazolyl, pyridyl, thiazolyl, thiadiazolyl, thienyl, furyl, pyrrolyl, pyrazinyl, pyrimidinyl, oxazolyl and isoxazolyl, and condensed aromatic heterocyclic group such as benzimidazolyl, imidazopyrimidinyl, imidazopyridinyl, imidazopyrazinyl, imidazopyridazinyl, benzothiazolyl, quinolyl, isoquinolyl, quinazolinyl and indolyl, among which five- or six-membered aromatic heterocyclic groups having i to 3 hetero atoms optically selected from a nitrogen atom, a sulfur atom and an oxygen atom (e.g., imidazolyl, triazolyl, thiazolyl, thiadiazolyl, thienyl, furyl, pyridyl or pyrimidinyl) are preferred.

Examples of the substituents in the optionally substituted aliphatic or aromatic hydrocarbon group or optionally substituted aromatic heterocyclic group are a hydroxy group, optionally esterified carboxy group (e.g., alkoxycarbonyl groups having 1 to 6 carbon atoms such as carboxy, methoxycarbonyl, ethoxycarbonyl and butoxycarbonyl), nitro group, amino group, acylamino group (e.g., alkanoyl amino groups having 1 to 10 carbon atoms such as acetylamino, propionylamino and butyrylamino), alkylamino group which is mono- or di-substituted with alkyl group having 1 to 10 carbon atoms (e.g., methylamino, dimethylamino, diethylamino or dibutylamino), optionally substituted five- or six-membered heterocyclic group (e.g., pyrrolidinyl, morpholino, piperidino, pirazolydinyl, perhydroazepinyl, piperazinyl, 4-benzylpiperazinyl, 4-acetylpiperazinyl, 4-(4-trifluoromethoxyphenyl)-1-piperazinyl, 4-[4-(1,1,2,2-tetrafluoroethoxy)phenyl]-1-piperazinyl, 4-[4-(2,2,3,3-tetrafluoropropoxy)phenyl]-1-piperazinyl, 4-[4-(2,2,2-trifluoroethoxy)phenyl]-1-piperazinyl, 4-[4-(2,2,3,3,3-pentafluoropropoxy)phenyl]-1-piperazinyl or 4-(4-trifluoromethylphenyl)-1-piperazinyl), alkoxy group having 1 to 6 carbon atoms (e.g., methoxy, ethoxy or butoxy), halogen atom (e.g., fluorine, chlorine or bromine), halogeno $C_{1-6}$ alkyl group (e.g., trifluoromethyl, dichloromethyl or trifluoroethyl), halogeno $C_{1-6}$ alkoxy group (e.g., trifluoromethoxy, 1,1,2,2-tetrafluoroethoxy, 2,2,2-trifluoroethoxy, 2,2,3,3-tetrafluoropropoxy, 2,2,3,3,3-pentafluoropropoxy, 2,2,3,3,4,4,5,5-octafluoropentoxy or 2-fluoroethoxy), oxo group, thioxo group, mercapto group, alkylthio group having 1 to 6 carbon atoms (e.g., methylthio, ethylthio or butylthio), alkylsulfonyl group having 1 to 6 carbon atoms (e.g., methanesulfonyl, ethanesulfonyl or butanesulfonyl) and alkanoyl group having 1 to 10 carbon atoms (e.g., acetyl, formyl, propionyl or butyryl).

Among the substituents in the saturated cyclic amide group represented by A, optionally substituted aliphatic hydrocarbon group, optionally substituted aromatic hydrocarbon group and optionally substituted aromatic heterocyclic group are preferably attached to a nitrogen atom which constitutes the broken line part in the ring of the above-mentioned saturated cyclic amide group.

Preferred examples of A are an unsubstituted saturated cyclic amide group, a saturated cyclic amide group substituted with an oxo group, a saturated cyclic amide group substituted with a halogenophenyl group, a saturated cyclic amide group substituted with halogenophenyl and oxo groups, a saturated cyclic amide group substituted with halogenated ($C_{1-6}$) alkylphenyl, a saturated cyclic amide group substituted with halogenated ($C_{1-6}$) alkylphenyl and oxo groups, a saturated cyclic amide group substituted with a halogenated ($C_{1-6}$) alkoxyphenyl, and a saturated cyclic amide group substituted with halogenated ($C_{1-6}$) alkoxyphenyl and oxo groups.

Examples of the unsubstituted saturated cyclic amide groups referred to hereinabove are 2-oxo-1-imidazolidinyl, 5-oxo-1-imidazolidinyl, 2-oxo-1-pyrrolidinyl, 3-oxo-2-pyrazolidinyl, 2-oxo-1-piperazinyl, 2-oxo-1-piperidinyl, 3-oxomorpholino and 2-oxo-1-perhydropyrimidinyl.

Examples of the saturated cyclic amide groups substituted with an oxo group are 2,4-dioxo-1-imidazolidinyl, 2,5-dioxo-1-imidazolidinyl, 2,4-dioxo-1-pyrrolidinyl, 3,5-dioxo-2-pyrazolidinyl, 2,3-dioxo-1-piperazinyl, 2,5-dioxo-1-piperazinyl and 2,3-dioxo-1-piperidinyl.

Preferably, the above-mentioned unsubstituted saturated cyclic amide group and saturated cyclic amide group substituted with an oxo group further contain a nitrogen atom in the ring in addition to a nitrogen atom bonding to a carbon bearing $R^1$ and $R^2$. The additional nitrogen atom preferably bonds to a substituent such as a halogenophenyl group, a halogeno $C_{1-6}$ alkylphenyl group and a halogeno $C_{1-6}$ alkoxyphenyl group as described below.

Examples of the saturated cyclic amide groups substituted with a halogenophenyl group are 3-halogenophenyl-2-oxo-1-imidazolidinyl, 3-halogenophenyl-2-oxo-1-pyrrolidinyl, 4-halogenophenyl-2-oxo-1-piperazinyl and 4-halogenophenyl-2-oxo-1-piperidinyl, among which 3-halogenophenyl-2-oxo-1-imidazolidinyl is preferable.

Examples of the saturated cyclic amide groups substituted with halogenophenyl and oxo groups are 3-halogenophenyl-2,4-dioxo-1-imidazolidinyl, 3-halogenophenyl-2,4-dioxo-1-pyrrolidinyl, 4-halogenophenyl-2,5-dioxo-1-piperazinyl, 4-halogenophenyl-2,3-dioxo-1-piperazinyl and 4-halogenophenyl-2,3-dioxo-1-piperidinyl, among which 3-halogenophenyl-2,4-dioxo-1-imidazolidinyl, 4-halogenophenyl-2,5-dioxo-1-piperazinyl and 4-halogenophenyl-2,3-dioxo-1-piperazinyl are preferable.

Examples of the saturated cyclic amide groups substituted with a halogenated ($C_{1-6}$) alkylphenyl are 3-halogenated ($C_{1-6}$) alkylphenyl-2-oxo-1-imidazolidinyl, 3-halogenated ($C_{1-6}$) alkylphenyl-2-oxo-1-pyrrolidinyl, 4-halogenated ($C_{1-6}$) alkylphenyl-2-oxo-1-piperazinyl and 4-halogenated ($C_{1-6}$) alkylphenyl-2-oxo-1-piperidinyl, among which 3-halogenated ($C_{1-6}$) alkylphenyl-2-oxo-1-imidazolidinyl is preferable.

Examples of the saturated cyclic amide groups substituted with halogenated ($C_{1-6}$) alkylphenyl and oxo groups are 3-halogenated ($C_{1-6}$) alkylphenyl-2,4-dioxo-1-imidazolidinyl, 3-halogenated ($C_{1-6}$) alkylphenyl-2,4-dioxo-1-pyrrolidinyl, 4-halogenated ($C_{1-6}$) alkylphenyl-2,5-dioxo-1-piperazinyl, 4-halogenated ($C_{1-6}$) alkylphenyl-2,3-dioxo-1-piperazinyl and 4-halogenated ($C_{1-6}$) alkylphenyl-2,3-dioxo-1-piperidinyl, among which 3-halogenated ($C_{1-6}$) alkylphenyl-2,4-dioxo-1-imidazolidinyl, 4-halogenated ($C_{1-6}$) alkylphenyl-2,5-dioxo-1-piperazinyl and 4-halogenated ($C_{1-6}$) alkylphenyl-2,3-dioxo-1-piperazinyl are preferable.

Examples of the saturated cyclic amide groups substituted with halogenated ($C_{1-6}$) alkoxyphenyl are 3-halogenated ($C_{1-6}$) alkoxyphenyl-2-oxo-1-imidazolidinyl, 3-halogenated ($C_{1-6}$) alkoxyphenyl-2-oxo-1-pyrrolidinyl, 4-halogenated ($C_{1-6}$) alkoxyphenyl-2-oxo-1-piperazinyl and 4-halogenated ($C_{1-6}$) alkoxyphenyl-2-oxo-1-piperidinyl, among which 3-halogenated ($C_{1-6}$) alkoxyphenyl-2-oxo-1-imidazolidinyl is preferable.

Examples of the saturated cyclic amide groups substituted with halogenated ($C_{1-6}$) alkoxyphenyl and oxo groups are 3-halogenated ($C_{1-6}$) alkoxyphenyl-2,4-dioxo-1-imidazolidinyl, 3-halogenated ($C_{1-6}$) alkoxyphenyl-2,4-dioxo-1-pyrrolidinyl, 4-halogenated ($C_{1-6}$) alkoxyphenyl-2,5-dioxo-1-piperazinyl, 4-halogenated ($C_{1-6}$) alkoxyphenyl-2,3-dioxo-1-piperazinyl and 4-halogenated ($C_{1-6}$) alkoxyphenyl-2,3-dioxo-1-piperizinyl, among which 3-halogenated ($C_{1-6}$) alkoxyphenyl-2,4-dioxo-1-imidazolidinyl, 4-halogenated ($C_{1-6}$) alkoxyphenyl-2,5-dioxo-1-piperazinyl and 4-halogenated ($C_{1-6}$) alkoxyphenyl-2,3-dioxo-1-piperazinyl are preferable.

More preferred examples of A are a saturated cyclic amide group substituted with a halogenophenyl group, a saturated cyclic amide group substituted with halogenophenyl and oxo groups, a saturated cyclic amide group substituted with a halogenated ($C_{1-6}$) alkylphenyl, a saturated cyclic amide group substituted with halogenated ($C_{1-6}$) alkylphenyl and oxo groups, a saturated cyclic amide group substituted with a halogenated ($C_{1-6}$) alkoxyphenyl and a saturated cyclic amide group substituted with halogenated ($C_{1-6}$) alkoxyphenyl and oxo groups.

Most preferred examples of A are 3-halogenophenyl-2-oxo-1-imidazolidinyl (e.g., 3-(2,4-difluorophenyl)-2-oxo-1-imidazolidinyl or 3-(4-fluorophenyl)-2-oxo-1-imidazolidinyl), 3-halogenated lower ($C_{1-4}$) alkylphenyl-2-oxo-1-imidazolidinyl (e.g., 3-(4-trifluoromethylphenyl)-2-oxo-1-imidazolidinyl), 3-halogenated lower ($C_{1-4}$) alkoxyphenyl-2-oxo-1-imidazolidinyl (e.g., 3-(4-trifluoromethoxyphenyl)-2-oxo-1-imidazolidinyl, 3-[4-(2,2,3,3-tetrafluoropropoxy)phenyl]-2-oxo-1-imidazolidinyl, 3-[4-(1,1,2,2-tetrafluoroethoxy)phenyl]-2-oxo-1-imidazolidinyl, 3-[4-(2,2,3,3,3-pentafluoropropoxy)phenyl]-2-oxo-1-imidazolidinyl or 3-[4-(-2,2,2-trifluoroethoxy)phenyl]-2-oxo-1-imidazolidinyl).

Particularly preferred examples of optionally-substituted saturated cylcic amide groups bonded through a nitrogen atom are a 3-substituted phenyl-2-oxo-1-imidazolidinyl of the formula:

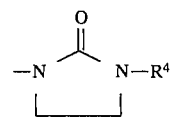

wherein $R^4$ is a substituted phenyl group, or a 4-substituted phenyl-2,5-dioxo-1-piperazinyl of the formula:

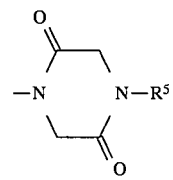

wherein $R^5$ has the same meaning as $R^4$.

Examples of the substituted phenyl groups represented by $R^4$ and $R^5$ are a halogenophenyl group, a halogenated ($C_{1-6}$) alkylphenyl group, a halogenated ($C_{1-6}$) alkoxyphenyl group, which are mentioned as the substituents in the saturated cyclic amide group.

The compound (I) can be also used as a salt thereof and examples of such salts are a pharmacologically-acceptable salts such as a salt with inorganic acid (e.g., hydrochloric acid, hydrobromic acid, sulfuric acid, nitric acid or phosphoric acid) and a salt with organic acid (e.g., acetic acid, tartaric acid, citric acid, fumaric acid, maleic acid, toluenesulfonic acid or methanesulfonic acid).

The compound represented by a formula (I) or a salt thereof (hereinafter, referred to as the compound of the present invention) has one or more asymmetric carbon(s) in its molecule and, therefore, there are two or more stereoisomers. Any of such stereoisomers as well as a mixture thereof is within a scope of the present invention. Among those, the optically active substances that when $R^1$ is a hydrogen atom and $R^2$ is a methyl group, both of the carbon atom to which the optionally-substituted phenyl group represented by Ar is bonded and another carbon atom to which $R^2$ is bonded are in the (R)-configurations are particularly preferred.

The compound of the present invention can be manufactured by, for example, reacting of a compound of the formula (II):

wherein the symbols have the same meanings as defined above, with a compound of the formula (III):

wherein the symbols have the same meanings as defined above, or a salt thereof, if necessary followed by treating with an acylating agent.

The reaction can be usually conducted out in a solvent which does not impede the reaction. Examples of the solvents which does not impede the reaction are water; ketones such as acetone; sulfoxides such as dimethyl sulfoxide; ethers such as diethyl ether, tetrahydrofuran and dioxane; nitriles such as acetonitrile; aromatic hydrocarbons such as benzene, toluene and xylene; halogenated hydrocarbons such as dichloromethane, chloroform and 1,2-dichloroethane; esters such as ethyl acetate; amides such as dimethylformamide, acetamide, dimethylacetamide and 1-methyl-2-pyrrolidinone; ureylenes such as 1,3-dimethyl-2-imidazolidinone; and the like. They may be used either singly or as a mixture thereof in a suitable mixing ratio.

Further, it is preferred that the above reaction is conducted out in the presence of a base such as alkali metal hydroxides (e.g., lithium hydroxide, potassium hydroxide or sodium hydroxide), alkali metal hydrides (e.g., potassium hydride or sodium hydride), alkali metal carbonates (e.g., lithium carbonate, sodium bicarbonate, cesium carbonate, potassium carbonate or sodium carbonate), organic acid salts (e.g., sodium acetate), alkali metal alcoholates (e.g., sodium methylate or potassium tert-butylate), tetrabutylammonium fluoride and bis(tri-n-butylstannyl)oxide.

Alternatively, the desired compound can be manufactured by the reaction in the above-mentioned solvent using a salt of the compound (III) with metal (e.g., alkali metal such as sodium and potassium) instead of the compound (III).

The amount of the base used is usually about 0.001 to 100 equivalents, preferably about 0.01 to 50 equivalents, to the compound (II).

The amount ot the compound (III) or salt thereof is about 1 to 100 equivalents, preferably about 1 to 50 equivalents, to the compound (II).

The reaction temperature is not particularly limited but, usually it is about 0° to 150° C., preferably about 10° to 120° C.

The reaction time is usually about several minutes to several ten hours (for example, from five minutes to fifty hours).

The compound of the present invention can be manufactured by, for example, reacting a compound of the formula (IV):

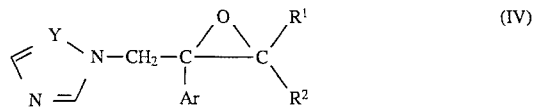

wherein the symbols have the same meanings as defined above, or the salt thereof with a compound of the formula (V):

wherein the symbols have the same meanings as defined above, or the salt thereof to give a compound of formula (I) in which $R^3$ is a hydrogen atom.

The above reaction can be usually conducted in a solvent which does not impede the reaction. Examples of such solvents are water; ketones such as acetone; sulfoxides such as dimethyl sulfoxide; ethers such as diethyl ether, tetrahydrofuran and dioxane; nitriles such as acetonitrile; aromatic hydrocarbons such as benzene, toluene and xylene; halogenated hydrocarbons such as dichloromethane, chloroform and 1,2-dichloroethane; esters such as ethyl acetate; amides such as dimethylformamide, acetamide, dimethylacetamide and 1-methyl-2-pyrrolidinone; ureylenes such as 1,3-dimethyl-2-imidazolidinone; and the like. They may be used either singly or as a mixture thereof in a suitable mixing ratio.

Further, it is preferred that the above reaction is conducted in the presence of a base such as alkali metal hydroxides (e.g., lithium hydroxide, potassium hydroxide or sodium hydroxide), alkali metal hydrides (e.g., potassium hydride or sodium hydride), alkali metal carbonates (e.g., lithium carbonate, sodium bicarbonate, cesium carbonate, potassium carbonate or sodium carbonate), organic acid salts (e.g., sodium acetate), alkali metal alcoholates (e.g., sodium methylate or potassium tert-butylate), tetrabutylammonium fluoride, bis(tri-n-buthylstannyl)oxide, and the like, among which tetrabutylammonium fluoride is preferred.

Alternatively, the desired compound can be manufactured by the reaction in the above-mentioned solvent using a salt of the compound (V) with metal (e.g., alkali metal such as sodium and potassium) instead of the compound (V).

The amount of the base is usually about 0.001 to 100 equivalents, preferably about 0.01 to 50 equivalents, to the compound of the formula (V).

The amount of the compound (V) or salt thereof is about 0.1 to 100 equivalents, preferably about 0.1 to 50 equivalents, to the compound (IV).

The reaction temperature is not particularly limited but, usually it is about 0° to 150° C. preferably about 10° to 120° C.

The reaction time is usually about several minutes to several ten hours (e.g., five minutes to fifty hours).

The compound of the formula (I) wherein A is an optionally-substituted 2-oxo-1-imidazolidinyl or a salt thereof can be manufactured by, for example, subjecting a compound of the formula (VI):

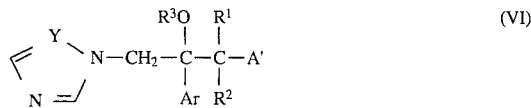

wherein A' is an optionally-substituted 2-oxo-2,3-dihydro-1H-imidazol-1-yl group and the other symbols have the same meanings as defined above, or a salt thereof to a catalytic reduction reaction.

The above-mentioned reaction is usually conducted in the presence of water or an organic solvent which does not impede the reaction such as ketones (e.g., acetone or methyl ethyl ketone), alcohols (e.g., methanol, ethanol, propanol, isopropyl alcohol or butanol), esters (e.g., ethyl acetate), hydrocarbons (e.g., benzene, toluene, hexane or xylene), organic carboxylic acids (e.g., acetic acid or propionic acid), and the like, which may be used either singly or as a mixture thereof. This reaction is usually conducted in the presence of a catalyst. With respect to the catalyst, a suitable metal catalyst such as palladium-carbon is used. This reduction reaction is conducted under from an atmospheric pressure to a pressure of up to about 150 kg/cm² at the temperature of from room temperature to about 100° C.

Examples of the salts of the above-mentioned starting compounds (III), (IV) and (VI) are the same as those of the compound (I).

When a compound of the formula (I) wherein $R^3$ is a hydrogen atom is obtained by the above-mentioned reactions, the compound or the salt thereof can be acylated to give another compound of the formula (I) wherein $R^3$ is an acyl group, by treating it with an appropriate acylating agent of $R^3X$ ($R^3$ is an aliphatic or aromatic hydrocarbon residue such as acetyl, propionyl, butyryl, ethoxycarbonyl, benzoyl and substituted benzoyl; and X is a leaving group such as a halogen atom, e.g., chlorine or bromine or activated ester group).

The above-mentioned reaction is usually conducted in the absence or presence of a solvent which does not impede the reaction. Examples of such solvents are ketones such as acetone; sulfoxides such as dimethyl sulfoxide; ethers such as diethyl ether, tetrahydrofuran and dioxane; nitriles such as acetonitrile; aromatic hydrocarbons such as benzene, toluene and xylene; halogenated hydrocarbons such as dichloromethane, chloroform and 1,2-dichloroethane; esters such as ethyl acetate; amides such as dimethylformamide, acetamide and demethylacetamide; ureylenes such as 1,3-dimethyl-2-imidazolidinone; and the like. For acceleration of the reaction rate, a base (e.g., dimethylaminopyridine, piridine, picolin or triethylamine) can be added to the reaction system.

The compound of the present invention can be isolated and purified from the reaction mixture by a known procedure per se such as extraction, concentration, neutralization, filtration, recrystallization, column chromatography and thin layer chromatography.

The compound of the present invention can have at least two stereoisomers. Each of such isomers and each of mixtures thereof is included in the concept of the present invention and, if desired, such an isomer can be manufactured separately. For example, a single isomer of the compound of the present invention can be obtained by the above-mentioned reaction starting from each single isomer of the starting compounds (II), (IV) and (VI). When the product is a mixture of two or more isomers, they may be separated into each isomer by a conventional separating method such as a method of producing salt with an optically-active acid (e.g., camphorsulfonic acid or tartaric acid) or by means of various types of chromatographies, fractional recrystallization and so on.

The salt of the compound (I) can be manufactured by a known method pe se such as by adding the above-mentioned inorganic or organic acid to the compound (I).

The starting compound (II) in the present invention wherein $R^1$ is a hydrogen atom, $R^2$ is a methyl group, the carbon to which Ar is bonded is in an (S)-configuration and the carbon to which $R^2$ is bonded is in an (R)-configuration (i.e., a compound (VII)) can be manufactured by a method as given in the following scheme.

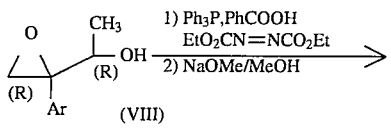

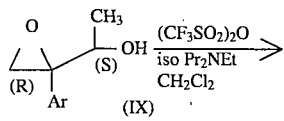

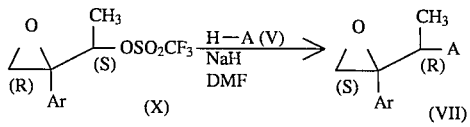

wherein Me is a methyl group, Et is a ethyl group, Pr is a propyl group, Ph is a phenyl group, DMF is dimethyl formamide and the other symbols have the same meanings as defined above.

The starting compound (VIII) in the scheme can be manufactured by a method as given in the following scheme.

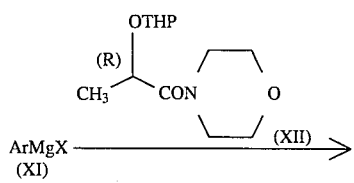

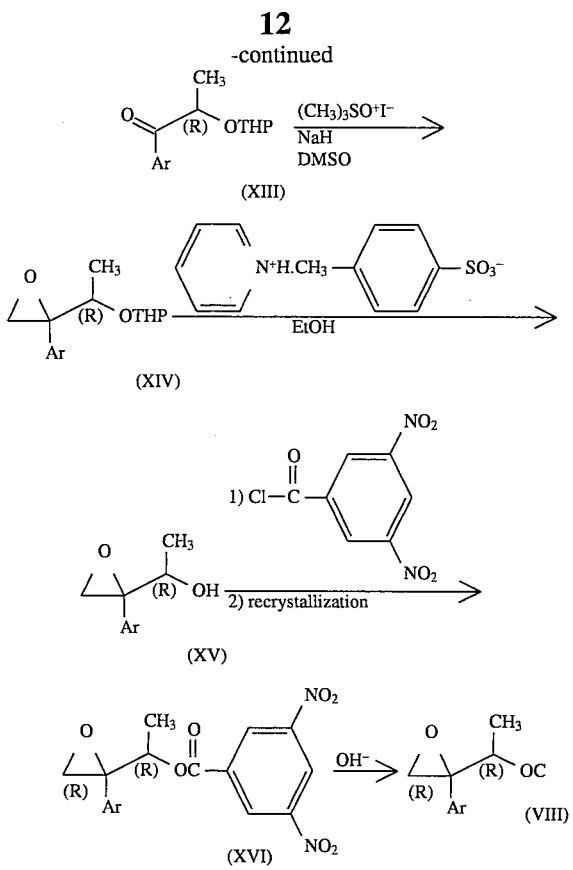

wherein THP is a tetrahydropyranyl group, DMSO is dimethylsulfoxide and the other symbols have the same meanings as defined above.

The starting compound (VI) in the present invention wherein $R^1$ is a hydrogen atom, $R^2$ is a methyl group, $R^3$ is a hydrogen atom and both a carbon to which Ar is bonded and a carbon to which $R^2$ is bonded are in (R)-configurations (i.e., a compound (XVII)) can be manufactured by, for example, a method as given in the following scheme.

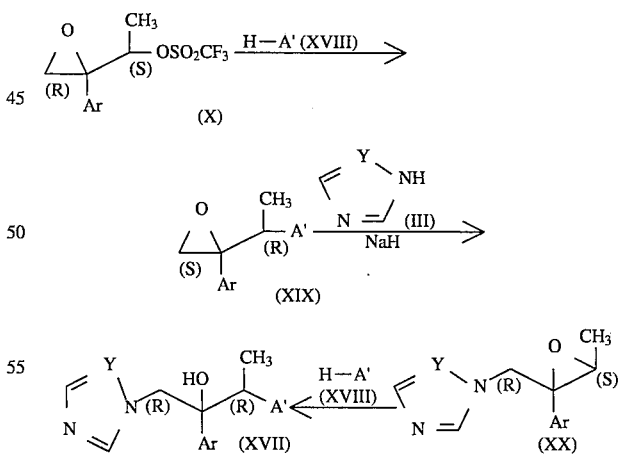

wherein the symbols have the same meanings as defined above.

The starting compound (XX) in the scheme can be synthesized by a method disclosed in EP0548553A or EP0421210A.

The starting compound (XVIII) in the present invention wherein A' is a 3-substituted-2-oxo-2,3-dihydro-1H-imidazol-1-yl group (i.e., a compound (XXI)) can be manufactured by, for example, a method as given in the following scheme.

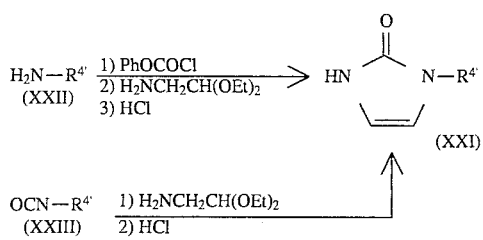

wherein $R^{4'}$ is a substituent in the above-mentioned A and the other symbols have the same meanings as defined above.

The compound (V) wherein A is a 3-substituted-2-oxo-1-imidazolidinyl (i.e., a compound (XXIV)) can be manufactured by, for example, a method as given in the following scheme.

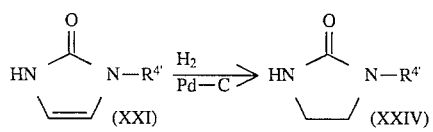

wherein the symbols have the same meanings as defined above.

The compound (V) wherein A is a 4-substituted-2,5-dioxo-1-piperazinyl (i.e., a compound (XXV)) can be manufactured by, for example, a method as given in the following scheme.

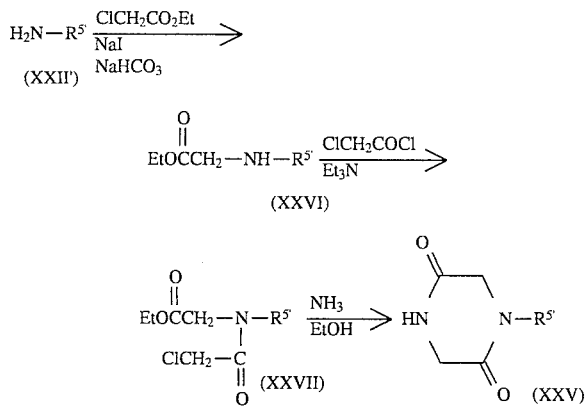

wherein $R^{5'}$ is a substituent in the above-mentioned A and the other symbols have the same meanings as defined above.

The compound (V) wherein A is a 4-substituted-2,3-dioxo-1-piperazinyl (i.e., a compound (XXVIII)) can be manufactured by a method as given in the following scheme.

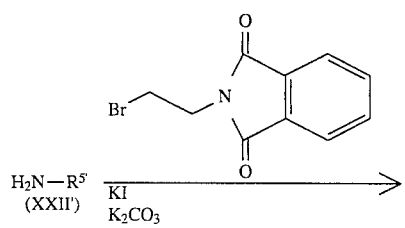

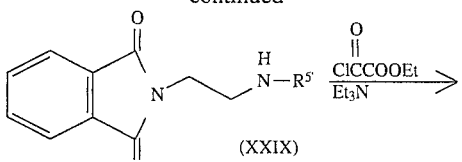

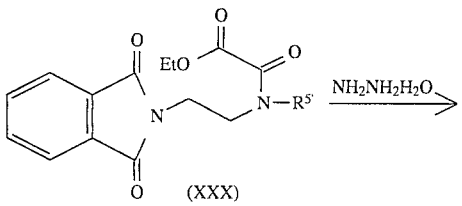

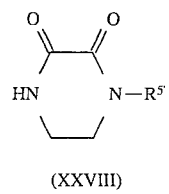

wherein the symbols have the same meanings as defined above.

Further, the intermediate compound (IX) in the present invention can be manufactured by, for example, a method as given in the following scheme.

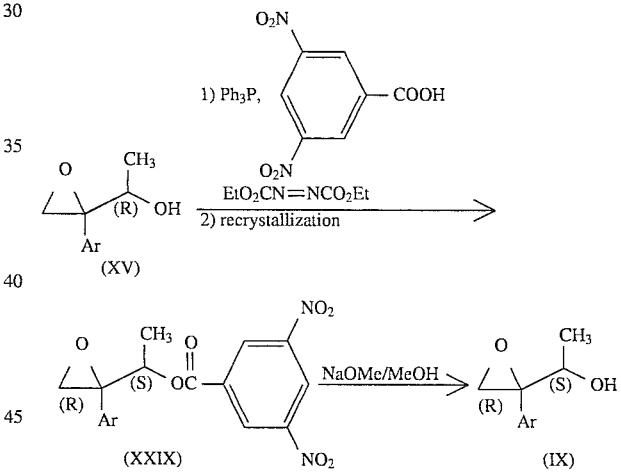

wherein the symbols have the same meanings as defined above.

The above-mentioned starting compounds can be isolated and purified from the reaction mixture by a known procedure per se such as extraction, concentration, neutralization, filtration, recrystallization, column chromatography, thin layer chromatograhy, etc.

The compound of the present invention has low toxicity and exhibits high antifungal activities with broad antifungal spectrum against, for example, microorganisms of genus Candida (e.g., *Candida albicans, Candida utilis, Candida grabrata* etc.), those of genus Aspergillus (e.g., *Aspergillus niger, Aspergillus fumigatus,* etc.), those of genus Cryptococcus (e.g., *Cryptococcus neoformans,* etc.), those of genus Tricophyton (e.g., *Trichophyton rubrum, Trichophyton mentagrophytes,* etc.), those of genus Microsporum (e.g., *Microsporum gypseum,* etc.) and the like and, therefore, it can be used for prevention and therapy of the fungal infections (e.g., candidiasis, histoplasmosis, aspergillosis, cryptococcosis, trichophytosis, microsporumosis, etc.) of mammals (e.g., human being, domestic animals, fowls, etc.). Further, the compound of the present invention can be also used as an antifungal preparation for agricultural use.

The starting compound (VI) for manufacturing the compound (I) of the present invention wherein $R^3$ is a hydrogen atom has also antifungal activities against the above-mentioned microorganisms.

When the compound of the present invention is administered to human being, it can be safely administered either orally or parenterally in the form of pharmaceutical compositions such as oral administration preparations (e.g., powders, granules, tablets, capsules, etc.), parenteral administration preparations [e.g., injections, external preparations (e.g., nasal or dermatological ones), suppositories (e.g., rectal or vaginal ones)], and the like in per se or by mixing with suitable pharmacologically-acceptable carriers, excipients, diluents, etc.

Those preparations can be manufactured by the methods which are known per se and commonly used in the manufacture of pharmaceutical preparations.

For example, the compound of the present invention can be made into injections such as aqueous injections together with dispersing agents (e.g., Tween 80 [Atlas Powder, U.S.A.], HCO60 [Nikko Chemicals, Japan], carboxymethylcellulose, sodium alginate, etc.), preservatives (e.g., methylparaben, propylparaben, benzyl alcohol, chlorobutanol, etc.), isotonic agents (e.g., sodium chloride, glycerol, sorbitol, glucose, etc.) and the like, or as oily injections by dissolving, suspending or emulsifying in a plant oil (e.g., olive oil, sesame oil, peanut oil, cotton seed oil, corn oil, etc.), propylene glycool and the like.

In the manufacture of preparations for oral administration, the compound of the present invention is molded with presure together, for example, with excipients (e.g., lactose, sugar, starch, etc.), disintegrating agents (e.g., starch, calcium carbonate, etc.), binders (e.g., starch, gum arabic, carboxymethylcellulose, polyvinylpyrrolidone, hydroxypropylcellulose, etc.), lubricants (e.g., talc, magnesium stearate, polyethylene glycol 6000, etc.) and the like followed, if necessary, by coating in accordance with a known method per se with an object of taste-masking or of providing the preparation with enteric or sustained release property. Examples of the coating agents are, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (Rohm, West Germany; a copolymer of methacrylic acid with acrylic acid) and pigments such as titanium oxide and red iron oxide.

In the case of preparation for external use, the compound of the present invention can be also made into a solid, semisolid or liquid preparation. For example, in the case of a solid preparation, the compound of the present invention is used as it is or mixed with excipients (e.g., glucose, mannitol, starch, microcrystalline cellulose, etc.), thickeners (e.g., natural gums, cellulose derivatives, acrylic acid polymers, etc.) and the like to give powdered compositions. In the case of a semisolid preparation, an aqueous or oily gel preparation or an ointment is preferred. In the case of a liquid preparation, the procedures are nearly the same as those in the case of injections to give oily or aqueous suspensions. The above-mentioned solid, semisolid or liquid preparations can be added with pH adjusting agents (e.g., carbonic acid, phosphoric acid, citric acid, hydrochloric acid, sodium hydroxide, etc.), antiseptics (e.g., p-hydroxybenzoates, chlorobutanol, benzalkonium chloride, etc.) or the like. More specifically, it can be used for sterilization or disinfection of skin or mucous membrane as an ointment containing, for example, about 0.1 to 100 mg of the compound of the present invention per gram using vaselin or lanoline as a base material.

In the case of suppositories, the compound of the present invention can be made into oily or aqueous suppositories in solid, semisolid or liquid. Examples of the oily base materials used therefor are higher fatty acid glycerides (e.g., cacao butter, Witepsols [Dynamite-Nobel], etc.), medium fatty acids (e.g., Migriols [Dynamite-Nobel], etc.), plant oil (e.g., sesame oil, soybean oil, cotton seed oil, etc.) and the like. Examples of the aqueous base material are polyethylene glycols, propylene glycols, etc., while those of the aqueous gel base materials are natural gums, cellulose derivatives, vinyl polymers, acrylic acid polymers, etc.

Dose of the compound of the present invention may vary depending upon the state of infection, the route of administration, etc. and, in the case of giving it to an adult patient (body weight: 50 kg) for the therapy of candidiasis for example, the dose is about 0.01 to 100 mg/kg/day, preferably about 0.1 to 50 mg/kg/day and, more preferably, about 0.1 to 20 mg/kg/day by oral route.

When the compound of the present invention is used as an agricultural antifungal agent, it is dissolved or dispersed in a suitable liquid carrier (e.g., solvents) or mixed or adsorbed with a suitable solid carrier (e.g., diluents or fillers) followed, if necessary, by adding emulsifier, suspending agent, spreader, penetrating agents, moisturizing agent, thickener, stabilizer, etc. to give the preparation such as emulsion, hydrating agent, powder, granules and the like. Such preparations can be prepared by a known method per se. The amount of the compound of the present invention is, for example in the case of a rice blast diseases, about 25 to 150 g, preferably about 40 to 80 g, per acre of irrigated rice field.

Examples of the liquid carriers are water, alcohols (e.g., methyl alcohol, ethyl alcohol, n-propyl alcohol, isopropyl alcohol, ethylene glycol, etc.), ethers (e.g., dioxane, tetrahydrofuran, etc.), aliphatic hydrocarbons (e.g., kerosene, lamp oil, fuel oil, etc.), aromatic hydrocarbons (e.g., benzene, toluene, etc.), halogenated hydrocarbons (e.g., methylene chloride, chloroform, etc.), acid amides (e.g., dimethylformamide, dimethylacetamide, etc.), esters (e.g., ethyl acetate, butyl acetate, etc.), nitriles (e.g., acetonitrile, propionitrile, etc.) and the like. They may be used either singly or as a mixture thereof in a suitable mixing ratio.

Examples of the solid carriers are plant powder (e.g., soybean powder, tabacco powder, wheat flour, etc.), mineral powder (e.g., kaolin, bentonite, etc.), alumina, sulfur powder, activated charcoal and the like. They may be used either singly or as a mixture thereof in a suitable mixing ratio.

EXAMPLES

The present invention will be further illustrated by way of the following reference examples, working examples and preparation examples. However, it is not intended to limit the scope of the present invention thereto.

$^1$H-NMR spectra were measured by a spectrometer of Varian Gemini 200 type (200 MHz) using tetramethylsilane as an internal standard. All δ value are given by ppm. In the mixing solvents, the figures given in ( ) are the mixing ratio of each of the solvents by volume. Unless otherwise specified, the symbol % means that by weight. In the silica gel chromatography, the ratio of the solvents is a ratio of the mixed solvents by volume.

The symbols used in the examples have the following meanings.

s: singlet; d: doublet; t: triplet; q: quartet; dd: double doublet; tt: triple triplet; m: multiplet; quintet:quintet; septet:septet; br: broad; J: coupling constant.

Reference Example 1

2-(2,4-Difluorophenyl)-2-[(1R)-1-(3,4,5,6-tetrahydro-2H-pyran-2-yl)oxyethyl]oxirane (82 g) (sythesized by a method disclosed in the Japanese Laid-Open Publication Hei-04/74168) and 6.3 g of pyridinium p-toluenesulfonte were dissolved in 600 ml of ethanol and the solution was stirred at 55° C. for one hour. The reaction solution was concentrated under reduced pressure. The residue was dissolved in one liter of ethyl acetate and the resulting solution was washed with water (2×200 ml). The aqueous layer was extracted with ethyl acetate (2×100 ml). The organic layers were combined, washed with a saturated aqueous solution of sodium chloride, dried over magnesium sulfate and distilled off under reduced pressure. The residue was purified by silica gel chromatography (eluent:hexane/ethyl acetate=10/1 to 8/1 to 3/1) to give 31.5 g of (1R)-1-[2-(2,4-difluorophenyl)-2-oxiranyl]ethanol as a pale yellow oil.

$^1$H-NMR (CDCl$_3$) δ: 1.14–1.23 (3H,m), 1.77, 2.22 (1H), 2.80, 2.92 (1H), 3.27–3.32 (1H), 4.00–4.20 (1H,m), 6.75–6.94 (2H,m), 7.36–7.48 (1H,m).

Reference Example 2

(1R)-1-[2-(2,4-Difluorophenyl)-2-oxiranyl]ethanol (31.5 g) and 40 g of 3,5-dinitrobenzoyl chloride were dissolved in 500 ml of methylene chloride and, with ice cooling, 24.1 ml of triethylamine was added dropwise thereinto. The reaction solution was stirred at room temperature for 3.5 hours, washed with 150 ml of water and then with 150 ml of 5% aqueous solution of sodium bicarbonate, dried over magnesium sulfate and concentrated under reduced pressure. The crystals separated out were collected by filtration and washed with methylene chloride. The mother liquor and the washing were combined and distilled off under reduced pressure, then 25 ml of ethyl acetate and 300 ml of methanol were added to the residue and the mixture was cooled with ice. The crystals separated out were collected by a filtration and recrystallized from a mixture of 25 ml of ethyl acetate and 250 ml of methanol to give 28.7 g of [(1R)-1-[(2R)-2-(2,4-difluorophenyl)-2-oxiranyl]ethyl]3,5-dinitrobenzoate as colorless needles.

mp 104°–107° C. (recrystallized from ethyl acetatehexane).

$^1$H-NMR (CDCl$_3$) δ: 1.46 (3H,dd,J=6.6 Hz,J=1.2 Hz), 3.01 (1H,d,J=4.6 Hz), 3.23 (1H,d,J=4.6 Hz), 5.33 (1H,q,J=6.6 Hz), 6.85–7.07 (2H,m), 7.54 (1H,m), 9.13 (2H,d,J=2.2 Hz), 9.25 (1H,t,J=2.2 Hz).

Reference Example 3

[(1R)-1-[(2R)-2-(2,4-Difluorophenyl)-2-oxiranyl]ethyl]3,5-dinitrobenzoate (50 g) was dissolved in two liters of methanol and, at room temperature, 255 ml of 1N sodium hydroxide was added dropwise thereinto. The reaction solution was stirred at room temperature for one hour and neutralized with 127 ml of 1N hydrochloric acid. Methanol was distilled off under reduced pressure, then one liter of ethyl acetate and 200 ml of water were added to the residue, and the mixture was extracted with ethyl acetate. The organic extract was washed with 200 ml of a saturated aqueous solution of sodium chloride, dried over magnesium sulfate and distilled off under reduced pressure. The residue was purified by silica gel chromatography (eluent: ethyl acetate/hexane=1/3) to give 25 g of (1R)-1-[(2R)-2-(2,4-difluorophenyl)-2-oxiranyl]ethanol as a pale yellow oil.

$^1$H-NMR (CDCl$_3$) δ: 1.17 (3H,dd,J=6.6 Hz,1.2 Hz), 2.05 (1H,br), 2.80 (1H,d,J=5.2 Hz), 3.30 (1H,d,J=5.2 Hz), 4.01–4.17 (1H,m), 6.75–6.93 (2H,m), 7.36–7.48 (1H,m).

Reference Example 4

To a solution of 16.1 g of (1R)-1-[(2R)-2-(2,4-difluorophenyl)-2-oxiranyl]ethanol in 320 ml of tetrahydrofuran were added, with ice cooling, 63.3 g of triphenylphosphine, 29.5 g of benzoic acid and 42.0 g of diethyl azodicarboxylate and the mixture was stirred at room temperature for six hours under an atmosphere of argon. To the reaction solution were added 800 ml of ethyl acetate and 500 ml of water to fractionate and the aqueous layer was extracted with 200 ml of ethyl acetate. The organic layers were combined, washed successively with water and a saturated aqueous solution of sodium chloride, then dried over magnesium sulfate and concentrated, The residue was purified by silica gel chromatography (eluent: hexane/ethyl acetate=15/1 to 7/1) to give 19.2 g of [(1S)-1-[(2R)-2-(2,4-difluororphenyl)-2-oxiranyl]ethyl]benzoate as a colorless oil.

$^1$H-NMR (CDCl$_3$) δ: 1.37 (3H,d,J=6.6 Hz), 2.90 (1H,d,J=5.2 Hz), 3.28 (1H,d,J=5.2 Hz), 5.36 (1H,q,J=6.6 Hz), 6.74–6.94 (2H,m), 7.38–7.60 (4H,m), 7.94–8.01 (2H,m).

IR $\nu^{neat}_{max}$cm$^{-1}$: 1725, 1615, 1600, 1505, 1450, 1425.

[(1S)-1-[(2R)-2-(2,4-Difluorophenyl)-2-oxiranyl]ethyl]benzoate (15.9 g) was dissolved in 800 ml of methanol, and 12.9 ml of 28% methanolic solution of sodium methylate was added thereto with ice cooling. The reaction solution was stirred for six hours at room temperature. To the reaction solution was added 63.2 ml of 1N hydrochloric acid and the solvent was distilled off under reduced pressure. The residue was purified by silica gel chromatography (eluent: hexane/ethyl acetate=6/1 to 2/1) to give 9.7 g of (1S)-1-[(2R)-2-(2,4-difluorophenyl)-2-oxiranyl]ethanol as a colorless oil.

$^1$H-NMR (CDCl$_3$) δ: 1.20 (3H,dd,J=6.4 Hz,2.2 Hz), 2.24 (1H,d,J=1 Hz), 2.92 (1H,d,J=5 Hz), 3.28 (1H,d,J=5 Hz), 4.12 (1H,q,J=6.4 Hz), 6.77–6.95 (2H, m), 7.34 (1H, m).

IR $\nu^{neat}_{max}$cm$^{-1}$: 3420, 2980, 1615, 1600, 1500, 1425.

Reference Example 5

2,4-Difluroaniline (25 g) and 25.2 g of pyridine were dissolved in 200 ml of dichloromethane and, with ice cooling, 33.3 g of phenyl chloroformate was added dropwise thereinto. The reaction solution was stirred with ice cooling for 30 minutes, washed with water and dried. The solvent was distilled off to give a mixture of phenyl 2,4-difluorophenylcarbamate and pyridine. To the mixture was added 30.7 g of 2-(diethoxy)ethylamine, and the resulting mixture was stirred at room temperature. The crystals separated out were collected by filtration and washed with petroleum ether to give 37.8 g of N-(2,2-diethoxyethyl)-N'-(2,4-difluorophenyl)urea as colorless crystals.

This urea compound (37.5 g) was dissolved in a mixture of 560 ml of methanol and 280 ml of water, 300 ml of 0.48M hydrochloric acid was added thereto and the mixture was stirred at room temperature for three days. The reaction solution was concentrated under reduced pressure and the crystals separated out were washed with a mixture of water and methanol (5:1) to give 22.8 g of 1-(2,4-difluorophenyl)-2-(1H,3H)-imidazolone as a colorless powder.

mp 192°–194° C.

Elemental analysis for $C_9H_6F_2N_2O$ Calcd (%): C 55.11, H 3.08, N 14.28 Found (%): C 55.14, H 3.29, N 14.18

Reference Examples 6–13

In the same manner as in Reference Example 5, the imidazolone derivatives shown in Table 1 were obtained.

TABLE 1

$$\underset{HN \underset{\diagdown\!\!=\!\!\diagup}{\phantom{XX}} N-R^4}{\overset{O}{\|}}$$

| Ref. Ex. No. | $R^4$ | mp (°C.) |
|---|---|---|
| 6 | –⟨phenyl⟩–OCF$_3$ | 145–146 |
| 7 | –⟨phenyl⟩–CF$_3$ | 170–171 |
| 8 | –⟨phenyl⟩–F | 166–167 |
| 9 | –⟨phenyl⟩–OCH$_2$CF$_2$CF$_2$H | 157–159 |
| 10 | –⟨phenyl⟩–OCF$_2$CF$_2$H | 161–163 |
| 11 | –⟨phenyl⟩–OCH$_2$CF$_2$CF$_3$ | 147–150 |
| 12 | –⟨phenyl⟩–OCH$_2$CF$_3$ | 145–151 |
| 13 | –⟨phenyl⟩–Cl | 176–178 |

Reference Example 14

Phenyl 2,4-difluorophenylcarbamate (5.0 g) and 4.2 g of glycine ethyl ester hydrochloride were dissolved in 30 ml of pyridine and the solution was heated at 80° C. for 14 hours. The reaction solution was concentrated under reduced pressure and to the residue were added 80 ml of ethyl acetate and 20 ml of water. The ethyl acetate layer was washed with 10 ml of an aqueous solution of sodium chloride, dried over anhydrous magnesium sulfate and concentrated under reduced pressure. Hexane (50 ml) was added to the residue and the solid separated out was collected by filtration to give 4.58 g of N-(2,4-difluorophenyl)-N'-ethoxycarbonylmethylurea as a colorless powder.

$^1$H-NMR (CDCl$_3$) δ: 1.29 (3H,t,J=7 Hz), 4.07 (2H,d,J=5.4 Hz), 4.24 (2H,q,J=7 Hz), 5.57 (1H,br), 6.75–6.90 (3H,m) 7.84–7.98 (1H,m).

The product (4.1 g) was dissolved in 80 ml of methanol, 3.0 g of 28% methanolic solution of sodium methoxide was added thereto and the mixture was stirred at room temperature for 2.5 hours. To the reaction solution was added 15 ml of 1N hydrochloric acid, the mixture was concentrated under reduced pressure, and then 20 ml of water was added to the residue. The mixture was extracted with 80 ml of ethyl acetate. The extract was washed successively with 20 ml of water and 20 ml of a saturated aqueous solution of sodium chloride and dried over anhydrous magnesium sulfate, and the solvent was distilled off under reduced pressure. The residue was crystallized from diethyl ether to give 1.0 g of 3-(2,4-difluorophenyl)-2,4-imidzolidinedione as a colorless powder.

mp 161°–170° C.

$^1$H-NMR (CDCl$_3$) δ: 4.20 (2H,s), 5.90 (1H,br), 6.95–7.10 (2H,m), 7.25–7.40 (1H,m).

Reference Example 15

1-[(4-(2,2,3,3-Tetrafluoropropoxy)phenyl]-2(1H,3H)-2-imidazolone (2.0 g) was dissolved in 10 ml of acetic acid, 0.5 g of 10% palladium-carbon was added thereto and the mixture was stirred for 7.5 hours in an atmosphere of hydrogen. The catalyst was filtered off, the catalyst was washed with acetic acid. The filtrate and the washing were combined and distilled off under reduced pressure. To the residue was added each 40 ml of water and ethyl acetate to fractionate, and the ethyl acetate layer was dried (over MgSO$_4$) and distilled off under reduced pressure. The resulting colorless crystals were washed with diisopropyl ether to give 1.86 g of 1-[4-(2,2,3,3-tetrafluoropropoxy)phenyl]-2-imidazolidinone as colorless crystals.

mp 180°–181° C.

$^1$H-NMR (CDCl$_3$) δ: 3.53–3.61 (2H,m), 3.87–3.95 (2H, m), 4.32 (2H,tt,J=11.8 Hz,1.6 Hz), 4.97 (1H,brs), 6.06 (1H,tt,J=53 Hz,5.0 Hz), 6.91 (2H,d,J=9.2 Hz), 7.47 (2H,d, J=9.2 Hz).

IR (KBr)ν$_{max}$: 3250, 1705, 1680, 1515, 1485 (cm$^{-1}$).

Elemental analysis for $C_{12}H_{12}F_4N_2O_2$ Calcd (%): C 49.32, H 4.14, N 9.59 Found (%): C 49.24, H 3.96, N 9.59

Reference Examples 16–19

In the same manner as in Reference Example 15, the imidazolidinones given in Table 2 were obtained.

TABLE 2

$$\underset{HN \underset{\diagdown\!\!-\!\!\diagup}{\phantom{XX}} N-R^4}{\overset{O}{\|}}$$

| Ref. Ex. No. | $R^4$ | mp (°C.) |
|---|---|---|
| 16 | –⟨phenyl⟩–OCF$_2$CF$_2$H | 169–171 |

TABLE 2-continued

|        | O       |
|        | ‖       |
|   HN   N—R⁴  |
|    \___/    |

| Ref. Ex. No. | R⁴ | mp (°C.) |
|---|---|---|
| 17 | —⟨phenyl⟩—OCH₂CF₂CF₃ | 190–192 |
| 18 | —⟨phenyl⟩—OCH₂CF₃ | 188–189 |
| 19 | —⟨phenyl⟩—Cl | 160–165 |

Reference Example 20

Diisopropylethylamine (0.51 ml) was added to a solution of 535 mg of (1S)-1-[(2R)-2-(2,4-difluorophenyl)-2-oxiranyl]ethanol in 15 ml of dichloromethane at −78° C. under an atmosphere of nitrogen and then 0.49 ml of trifluoromethanesulfonic acid anhydride was added dropwise thereinto over the period of three minutes. The mixture was stirred at −78° C. for 20 minutes, then at −20° C. for 20 minutes and the reaction solution was concentrated to about 9 ml at −10° C. The concentrated solution was subjected to flush column chromatography using silica gel (3.2×4 cm) and eluted with dichloromethane-hexane (1:1). The fraction containing the product was concentrated to about 3 ml. The residue was added, at −10° C., to a solution of sodium salt of 1-(4-trifluoromethylphenyl)-2(1H,3H)-imidazolone prepared from 606 mg of 1-(4-trifluoromethylphenyl)-2(1H, 3H)-imidazolone, 3 ml of dimethylformamide and 85 mg of 60% sodium hydride in oil and the mixture was stirred for ten minutes. The reaction solution was stirred at 0° C. for 20 minutes. Water (30 ml) was added to the reaction solution and the mixture was extracted with 30 ml of ethyl acetate four times. The ethyl acetate layer was washed successively with 20 ml of water twice and a saturated aqueous solution of sodium chloride once, and dried over anhydrous magnesium sulfate. The solvent was distilled off under reduced pressure to give a colorless oily product. This product was purified by silica gel chromatography (eluent: hexane/ethyl acetate=3/1 to 2/1 to 1/1) to give 362 mg of 1-[(1R,2S)-2-(2,4-difluorophenyl)- 2,3-epoxy-1-methylpropyl]-3-(4-trifluoromethylphenyl)-2(1H,3H)-imidazolone and 209 mg of (2R)-2-(2,4-difluorophenyl)-2-[(1R)-1-[1-(4-trifluoromethylphenyl)-2-imidazolyloxy]ethyl]oxirane.

1-[(1R,2S)-2-(2,4-difluorophenyl)-2,3-epoxy-1-methylpropyl]-3-(4-trifluoromethylphenyl)-2(1H,3H)-imidazolone: colorless prisms.

mp 135°–136° C.

¹H-NMR (CDCl₃) δ: 1.37 (3H,d,J=7.2 Hz), 2.72 (1H,d, J=4.4 Hz), 2.82 (1H,d,J=4.4 Hz), 5.09 (1H,q,J=7.2 Hz), 6.50 (1H,d,J=3.2 Hz), 6.64 (1H,d,J=3.2 Hz), 6.80–6.97 (2H,m), 7.35–7.50 (1H,m), 7.69 (2H,d,J=8.4 Hz), 7.82 (2H,d,J=8.4 Hz).

60% Sodium hydride in oil (65 mg) was dispersed in 4 ml of dimethylformamide, and 118 mg of 1,2,4-triazole was added thereto with ice cooling. The resulting mixture was stirred at room temperature for ten minutes. The solution of 362 mg of 1-[(1R,2S)-2-(2,4-difluorophenyl)-2,3-epoxy-1-methylpropyl]-3-(4-trifluoromethylphenyl)-2(1H,3H)-imidazolone prepared hereinabove in 2 ml of dimethylformamide was added thereto and the resulting mixture was heated at 50° C. for five hours. After cooling, to the reaction solution was added 8 ml of cold water and 40 ml of ethyl acetate to fractionate and the aqueous layer was extracted with ethyl acetate twice. The ethyl acetate layers were combined, washed with water and a saturated aqueous solution of sodium chloride successively, dried over anhydrous magnesium sulfate and distilled off under reduced pressure. The residue was purified by silica gel chromatography (eluent: ethyl acetate/hexane=1/1 to 2/1 to ethyl acetate) to give 350 mg of 1-[(1R,2S)-2-(2,4-difluorophenyl)-2-hydroxy-1-methyl-3-(1H-1,2,4-triazol-1-yl)propyl]-3-(4-trifluoromethylphenyl)-2(1H,3H) -imidazolone as a colorless powder.

¹H-NMR (CDCl₃) δ: 1.21 (3H,d,J=7.2 Hz), 4.19 (1H,d, J=14.2 Hz), 5.00 (1H,q,J=7.2 Hz), 5.11 (1H,d,J=14.2 Hz), 5.46 (1H,s), 6.71 (1H,d,J=3.2 Hz), 6.83 (1H,d,J=3.2 Hz) 6.72–6.90 (2H,m), 7.40–7.56 (1H,m), 7.72 (2H,d,J=8.4 Hz), 7.75 (1H,s), 7.83 (2H,d,J=8.4 Hz), 7.84 (1H,s).

IR ν$^{neat}_{max}$ cm⁻¹: 3404, 3383, 3000, 1693, 1618, 1599, 1524, 1500, 1429, 1327.

Elemental analysis for $C_{22}H_{18}F_5N_5O_2$ Calcd (%): C 55.12, H 3.78, N 14.61 Found (%): C 54.81, H 3.97, N 14.39

Reference Examples 21–23

The following compounds were prepared by the same manner as in Reference Example 20.

Reference Example 21

1-[(1R,2R)-2-(2,4-Difluorophenyl)-2-hydroxy-1-methyl-3-(1H-1,2,4-triazol-1-yl)propyl]-3-(2,4-difluorophenyl)-2(1H,3H)-imidazolone.

Colorless powdery crystals; yield: 416 mg (66%).

mp 134°–136° C.

¹H-NMR (CDCl₃) δ: 1.21 (3H,d,J=7 Hz), 4.19 (1H,d,J= 14.4 Hz), 4.95 (1H,q,J=7 Hz), 5.11 (1H,d,J=14.4 Hz), 5.52 (1H,br), 6.52 (1H,t,J=2.6 Hz), 6.70–6.86 (3H,m), 6.92–7.06 (2H,m), 7.40–7.68 (2H,m), 7.74 (1H,s), 7.85 (1H,s).

Reference Example 22

1-[(1R,2R) -2-(2,4-Difluorophenyl)-2-hydroxy-1-methyl-3-(1H-1,2,4-triazol-1-yl)propyl]-3-(4-trifluoromethoxyphenyl)-2(1H,3H)-imidazolone.

Colorless powder; yield: 500 mg (71%).

¹H-NMR (CDCl₃) δ: 1.20 (3H,d,J=7 Hz), 4.19 (1H,d,J= 14.4 Hz), 4.97 (1H,q,J=7 Hz), 5.10 (1H,d,J=14.4 Hz), 5.51 (1H,br), 6.39 (1H,d,J=3.2 Hz), 6.64 (1H,d,J=3.2 Hz), 6.70–6.86 (2H,m), 7.31 (2H,d,J=9 Hz), 7.38–7.54 (1H,m), 7.69 (2H,d,J=9 Hz), 7.74 (1H,s), 7.84 (1H,s).

Reference Example 23

1-[(1R,2R)-2-(2,4-Difluorophenyl)-2-hydroxy-1-methyl-3-(1H-1,2,4-triazol-1-yl)propyl]-3-(4-fluorophenyl)-2(1H, 3H)-imidazolone.

Colorless powder; yield: 971 mg (74%).

¹H-NMR (CDCl₃) δ: 1.20 (3H,d,J=7 Hz), 4.20 (1H,d,J= 14.2 Hz), 4.95 (1H,q,J=7 Hz), 5.10 (1H,d,J=14.2 Hz), 5.58 (1H,br), 6.60 (1H,d,J=3.2 Hz), 6.74 (1H,d,J=3.2 Hz), 6.70–6.88 (2H,m), 7.05–7.20 (2H,m), 7.40–7.65 (3H,m), 7.73 (1H,s), 7.85 (1H,s).

Reference Example 24

To a solution of 1.36 g of (1S)-1-[(2R)-2-(2,4-difluorophenyl)-2-oxiranyl]ethanol in 30 ml of dichloromethane was added 1.31 ml of diisopropylethylamine at −60° C. under an atmosphere of nitrogen and then 1.26 ml of trifluoromethanesulfonic acid anhydride was added dropwise thereinto over the period of three minutes. The mixture was stirred at −60° C. for 20 minutes, then at −20° C. for 20 minutes. The reaction solution was subjected to flush chromatography using 27 g of silica gel and eluted with 220 ml of dichloromethane-hexane (1:1). The fraction containing the product was concentrated to about 9 ml and the residue was added to a mixture of 1.15 g of 3-(2,4-difluorophenyl)-2,4-imidazolidinedione, 18 ml of dimethylformamide and 0.20 g of 60% sodium hydride in oil at −10° C. The resulting mixture was stirred for 20 minutes and then for 20 minutes at 0° C. Water (20 ml) was added thereto and the mixture was extracted with 100 ml of ethyl acetate. The ethyl acetate layer was washed with 20 ml of a saturated aqueous solution of sodium chloride, dried over anhydrous magnesium sulfate and distilled off under reduced pressure. The residue was purified by silica gel column chromatography (eluent: hexane/ethyl acetate=2/1) to give 1.25 g of 1-[(1R,2S)-2-(2,4-difluorophenyl)-2,3-epoxy-1-methylpropyl]-3-(2,4-difluorophenyl)-2,4-imidazolidinedione as a white solid.

mp 124°–125° C. (recrystallized from ethyl acetatehexane).

$^1$H-NHR (CDCl$_3$) δ: 1.30 (3H,d,J=7.2 Hz), 2.81 (1H,d,J=4.6 Hz), 3.08 (1H,d,J=4.6 Hz), 4.06 (1H,d,J=17.8 Hz), 4.22 (1H,d,J=17.8 Hz), 4.97 (1H,q,J=7.2 Hz), 6.78–7.04 (4H,m), 7.20–7.45 (2H,m).

Reference Examples 25–29

The following compounds were prepared by the same manner as in Reference Example 24.

Reference Example 25

1-[(1R,2S)-2-(2,4-Difluorophenyl)-2,3-epoxy-1-methylpropyl]-3-[4-(2,2,3,3-tetrafluoropropoxy)phenyl]-2-imidazolidinone.

Colorless powder.

$^1$H-NMR (CDCl$_3$) δ: 1.21 (3H,d,J=7.2 Hz), 2.75 (1H,d,J=7.0 Hz), 3.15 (1H,d,J=7.0 Hz), 3.42–3.64 (2H,m), 3.71–3.81 (2H,m), 4.32 (2H,tt,J=12 Hz,1.4 Hz), 4.80 (1H,q,J=7.2 Hz), 6.06 (1H,tt,J=53 Hz,5 Hz), 6.76–6.9 (2H,m), 6.91 (2H,d,J=9.2 Hz), 7.35–7.5 (1H,m), 7.48 (2H,d,J=9.2 Hz).

Reference Example 26

1-[(1R,2S)-2-(2,4-Difluorophenyl)-2,3-epoxy-1-methylpropyl]-3-[4-(1,1,2,2-tetrafluoroethoxyphenyl]-2-imidazolidinone.

Colorless powder.

$^1$H-NMR (CDCl$_3$) δ: 1.22 (3H,d,J=7.4 Hz), 2.75 (1H,d,J=5 Hz), 3.14 (1H,d,J=5 Hz), 3.44–3.65 (2H,m), 3.73–3.84 (2H,m), 4.80 (1H,q,J=7.4 Hz), 5.89 (1H,tt,J=53 Hz,2.8 Hz), 6.77–6.93 (2H,m), 7.17 (2H,d,J=9 Hz), 7.34–7.46 (1H,m), 7.55 (2H,d,J=9 Hz).

IR (KBr) ν$_{max}$: 1680, 1615, 1510, 1485, 1425 (cm$^{-1}$).

Reference Example 27

1-[(1R,2S)-2-(2,4-Difluorophenyl)-2,3-epoxy-1-methylpropyl]-3-[4-(2,2,3,3,3-pentafluoropropoxy)phenyl]-2-imidazolidinone.

Colorless prisms.

mp 141°–144° C. (ethyl acetate-hexane).

$^1$H-NMR (CDCl$_3$) δ: 1.22 (3H,d,J=7 Hz), 2.75 (1H,d,J=5.0 Hz), 3.15 (1H,d,J=5.0 Hz), 3.42–3.64 (2H,m), 3.73–3.82 (2H,m), 4.39 (2H,dt,J=12.4 Hz,1.2 Hz), 4.80 (1H,q,J=7 Hz), 6.77–6.90 (2H,m), 6.92 (1H,d,J=9.2 Hz), 7.34–7.42 (1H,m), 7.48 (2H,d,J=9.2 Hz).

Elemental analysis for C$_{22}$H$_{19}$F$_7$N$_2$O$_3$ Calcd (%): C 53.66, H 3.89, N 5.69 Found (%): C 53.37, H 3.74, N 5.62

IR (KBr) νmax: 1700, 1520, 1485, 1430, 1265 (cm$^{-1}$).

Reference Example 28

1-[(1R,2S)-2-(2,4-Difluorophenyl)-2,3-epoxy-1-methylpropyl]-3-[4-(2,2,2-trifluoroethoxy)phenyl]-2-imidazolidinone.

Colorless needles.

mp 131°–132° C. (diethyl ether).

$^1$H-NMR (CDCl$_3$) δ: 1.21 (3H,d,J=7.2 Hz), 2.75 (1H,d,J=5 Hz), 3.15 (1H,d,J=5 Hz), 3.42–3.64 (2H,m), 3.73–3.82 (2H,m), 4.32 (2H,q,J=8.2 Hz), 4.80 (1H,q,J=7.2 Hz), 6.77–6.88 (2H,m), 6.92 (2H,d,J=9 Hz), 7.34–7.44 (1H,m), 7.48 (2H,d,J=9 Hz).

Elemental analysis for C$_{21}$H$_{19}$F$_5$NO$_3$ Calcd (%): C 57.02, H 4.33, N 6.33 Found (%): C 57.33, H 4.06, N 6.39

IR (KBr) νmax: 1695, 1515, 1485, 1425, 1265, 1240 (cm$^{-1}$).

Reference Example 29

1-(4-Chlorophenyl)-3-[(1R,2S)-2-(2,4-difluorophenyl)-2,3-epoxy-1-methylpropyl]-2-imidazolidinone.

Colorless needles.

mp 130°–131° C. (ethyl acetate-hexane).

$^1$H-NMR (CDCl$_3$) δ: 1.22 (3H,d,J=7 Hz), 2.75 (1H, d, J=5 Hz), 3.14 (1H,d,J=5 Hz), 3.43–3.65 (2H,m), 3.73–3.82 (2H, m), 4.80 (1H,q,J=7 Hz), 6.77–6.93 (2H,m), 7.28 (2H,d,J=9 Hz), 7.34–7.54 (1H,m), 7.49 (2H,d,J=9 Hz).

Elemental analysis for C$_{19}$H$_{17}$ClF$_2$N$_2$O$_2$ Calcd (%): C 60.24, H 4.52, N 7.40 Found (%): C 60.45, H 4.38, N 7.45

IR (KBr) νmax: 1700, 1615, 1600, 1500, 1425, 1270 (cm$^{-1}$).

Reference Example 30

A mixture of 8.6 g of 4-(2,2,3,3-tetrafluoropropoxy)aniline, 4.8 g of ethyl chloroacetate, 4.8 g of sodium bicarbonate, 3.0 g of sodium iodide and 300 ml of acetone was refluxed for 21 hours. The solvent was distilled off under reduced pressure and 200 ml of ice water and 200 ml of dichloromethane were added to the residue to fractionate. The dichloromethane layer was washed with water, dried over anhydrous magnesium sulfate and distilled off under reduced pressure. The residue was purified by silica gel column chromatography (eluted with ethyl acetate:hexane [1:3 v/v]) to give 9.4 g of N-ethoxycarbonylmethyl-4-(2,2,3,3-tetrafluoropropoxy)aniline as pale yellow crystals.

To a mixture of 2.1 g of the resulting N-ethoxycarbonylmethyl-4-(2,2,3,3-tetrafluoropropoxy)aniline, 1.1 ml of triethylamine and 50 ml of dichloromethane was added dropwise a solution of 0.6 ml of chloroacetyl chloride in 6 ml of dichloromethane with ice cooling and the resulting mixture was stirred at room temperature for five hours. To the reaction solution was added 50 ml of dichloromethane and 100 ml of ice water to factionate. The dichloromethane layer was washed with water and dried over anhydrous magnesium sulfate. The solvent was distilled off under reduced pressure and the residue was purified by silica gel column chromatography (eluted with ethyl acetate:hexane [1:2 v/v]) to give 2.4 g of N-chloroacetyl-N-ethoxycarbonylmethyl-4-(2,2,3,3-tetrafluoropropoxy)aniline as a yellow oily substance.

The resulting N-chloroacetyl-N-ethoxycarbonylmethyl-4-(2,2,3,3-tetrafluoropropoxy)aniline (1.9 g) was dissolved in 20 ml of 10.5% ammonia-ethanol and the solution was stirred at 60° C. for four hours. After cooling, the crystals separated out therefrom were collected by filtration and washed with cold ethanol to give 1.5 g of 1-[4-(2,2,3,3-tetrafluoropropoxy)phenyl]-2,5-piperazinedione as colorless crystals.

$^1$H-NMR (d$_6$-DMSO) δ: 3.95 (2H,s), 4.20 (2H,s), 4.60 (2H,t,J=14 Hz), 6.67 (1H,tt,J=52 Hz,5.4 Hz), 7.08 (2H,d,J=9 Hz), 7.30 (2H,d,J=9 Hz), 8.27 (1H, brs).

Elemental analysis for $C_{13}H_{12}F_4N_2O_3$ Calcd (%): C 48.76, H 3.78, N 8.75 Found (%): C 48.99, H 3.65, N 8.88.

SIMS (MH$^+$): 321.

IR (KBr) νmax: 3440, 3250, 1670, 1650, 1510, 1330 (cm$^{-1}$).

Reference Example 31

1-[(1R,2S)-2-(2,4-Difluorophenyl)-2,3-epoxy-1-methylpropyl]-4-[4-(2,2,3,3-tetrafluoropropoxy)phenyl]-2,5-piperazinedione was obtained by the same manner as in Reference Example 24.

Colorless powdery crystals.

$^1$H-NMR (CDCl$_3$) δ: 1.25 (3H,d,J=7.2 Hz), 2.85 (1H,d,J=5 Hz) 3.10 (1H,d,J=5 Hz), 4.07 (1H,d,J=17 Hz), 4.21 (1H,d,J=17 Hz), 4.23 (1H,d,J=16 Hz), 4.34 (1H,d,J=16 Hz), 4.36 (2H,t,J=12 Hz), 5.37 (1H,q,J=7.2 Hz), 6.06 (1H,tt,J=53 Hz,4.8 Hz), 6.78–6.95 (2H,m), 6.98 (2H,d,J=9 Hz), 7.23 (2H,d,J=9 Hz), 7.35–7.47 (1H,m).

mp 155°–156° C. (ethyl acetate-hexane).

Elemental analysis for $C_{23}H_{20}F_6N_2O_4$ Calcd (%): C 54.99, H 4.01, N 5.58 Found (%): C 54.77, H 4.03, N 5.36

Reference Example 32

1-(4-Trifluoromethylphenyl)-2(1H,3H)-imidazolone (1.15 g) was dissolved in 20 ml of acetic acid. 10% Palladium-carbon (0.3 g) was added thereto and the mixture was stirred under a hydrogen stream for six hours. The catalyst was filtered off, the solvent was distilled off and the residue was recrystallized from ethyl acetate-diisopropyl ether to give 0.95 g of 1-(4-trifluoromethylphenyl)-2-imidazolidinone as colorless prisms.

mp 169°–171° C. (ethyl acetate-diisopropyl ether).

$^1$H-NMR (CDCl$_3$) δ: 3.63 (2H,t,J=8 Hz), 3.99 (2H,t,J=8 Hz), 4.95 (1H,br), 7.59 (2H,d,J=9 Hz), 7.68 (2H,d,J=9 Hz).

Elemental analysis for $C_{10}H_9F_3N_2O$ Calcd (%): C 52.18, H 3.94, N 12.17 Found (%): C 51.94, H 3.89, N 12.23

Reference Example 33

1-[(1R,2S)-2-(2,4-Difluorophenyl)-2,3-epoxy-1-methylpropyl]-3-(4-trifluoromethylphenyl)-2-imidazolidinone was obtained as a colorless powder by the same manner as in Reference Example 24.

$^1$H-NMR (CDCl$_3$) δ: 1.24 (3H,d,J=7.2 Hz), 2.76 (1H,d, J=4.8 Hz), 3.14 (1H,d,J=4.8 Hz), 3.48–3.70 (2H,m), 3.78–3.90 (2H,m), 4.83 (1H,q,J=7.2 Hz), 6.78–6.95 (2H,m), 7.35–7.48 (1H,m), 7.57 (2H,d,J=8.8 Hz), 7.67 (2H,d,J=8.8 Hz).

Reference Example 34

In the same manner as in Reference Example 30, starting from 4-(1,1,2,2-tetrafluoroethoxy)aniline, 1-[4-(1,1,2,2-tetrafluoroethoxy)phenyl]-2,5-piperazinedione was obtained as colorless crystals.

$^1$H-NMR (DMSO-d$_6$) δ: 3.97 (2H,s), 4.27 (2H,s), 6.81 (1H,tt,J=52 Hz,3 Hz), 7.32 (2H,d,J=9 Hz), 7.46 (2H,d,J=9 Hz), 8.31 (1H,br).

mp >250° C.

Elemental analysis for $C_{12}H_{10}F_4N_2O_3$ Calcd (%): C 47.07, H 3.29, N 9.15 Found (%): C 46.89, H 3.26, N 9.08

Reference Example 35

In the same manner as in Reference Example 24, 1-[(1R,2S)-2-(2,4-difluorophenyl)-2,3-epoxy-1-methylpropyl]-4-[4-(1,1,2,2-tetrafluoroethoxy)phenyl]-2,5-piperazinedione was obtained.

Colorless powdery crystals.

$^1$H-NMR (CDCl$_3$) δ: 1.25 (3H,d,J=7 Hz), 2.85 (1H,d,J=5 Hz), 3.09 (1H,d,J=5 Hz), 4.08 (1H,d,J=17 Hz), 4.22 (1H,d, J=17 Hz), 4.26 (1H,d,J=16 Hz), 4.37 (1H,d,J=16 Hz), 5.36 (1H,q,J=7 Hz), 5.92 (1H,tt,J=53 Hz,3 Hz), 6.78–6.95 (2H, m), 7.29 (4H,s), 7.30–7.47 (1H,m).

mp 168°–170° C.

Elemental analysis for $C_{22}H_{18}F_6N_2O_4$ Calcd (%): C 54.11, H 3.71, N 5.74 Found (%): C 54.08, H 3.75, N 5.64

Reference Example 36

A mixture of 4-(2,2,3,3-tetrafluoropropoxy)aniline (7.4 g), N-(2-bromoethyl)phthalimide (9.0 g), potassium bicarbonate (6.9 g), potassium iodide (5.5 g) and N,N-dimethylformamide (80 ml) are refluxed for 22 hours. The solvent was distilled off under reduced pressure. To the residue, ice-water (200 ml) and ethyl acetate (200 ml) were added and fractionated. The ethyl acetate layer was washed with water, dried over anhydrous magnesium sulfate and distilled off under reduced pressure. The residue was purified by silica gel chromatography (eluate; ethyl acetate:hexane=1:2 v/v) and recrystallized from ethyl acetate-diisopropyl ether to give N-(2-phthalimido)ethyl-4-(2,2,3,3-tetrafluoropropoxy)aniline (5.4 g) as white crystals.

To the mixture of the obtained N-(2-phthalimido)ethyl-4-(2,2,3,3-tetrafluoropropoxy)aniline (3.2 g), triethylamine (1.2 ml) and dichloromethane (60 ml), was added dropwise a solution of ethyl chloroglyoxylate (0.9 ml) in dichloromethane (10 ml) at −65° C. The reaction solution was stirred for 1 hour at −40° C., and then ice-water (50 ml) was added thereto to fractionate. The dichloromethane layer was washed with water and dried over anhydrous magnesium sulfate. The solvent was distilled off under reduced pressure. The residue was recrystallized from ethyl acetate-hexane to give N-ethoxalyl-N-(2-phthalimido)ethyl-4-(2,2,3,3-tetrafluoropropoxy)aniline (3.1 g) as colorless powdery crystals.

The mixture of the obtained N-ethoxalyl-N-(2-phthalimido)ethyl-4-(2,2,3,3-tetrafluoropropoxy)aniline (3.4 g), hydradine hydrate (0.7 ml) and ethanol (80 ml) was refluxed for 9 hours. The crystals separated out were filtered off before cooling and the solvent of the filtrate was distilled off under reduced pressure. Water (150 ml) and ethyl acetate (300 ml) were added to the residue to fractionate. The ethyl acetate layer was washed with 5% aqueous solution of sodium bicarbonate and then with a saturated aqueous solution of sodium chloride, and dried over anhydrous magnesium sulfate. The solvent was distilled off under reduced pressure. The residue was purified by silica gel chromatography (eluent; ethyl acetate:dichloromethane:methanol=7:7:1 v/v) to give 1-[4-(2,2,3,3-tetrafluoropropoxy)phenyl]-2,3-piperazinedione (0.8 g) as a colorless powder.

$^1$H-NMR (DMSO-d$_6$) δ: 3.44–3.55 (2H,m), 3.83–3.89 (2H,m), 4.61 (2H,t,J=13 Hz), 6.68 (1H,tt,J=52 Hz,6 Hz), 7.09 (2H,d,J=9 Hz), 7.34 (2H,d,J=9 Hz), 8.73 (1H,br).

Elemental analysis for $C_{13}H_{12}F_4N_2O_3$ Calcd (%): C 48.76, H 3.78, N 8.75 Found (%): C 48.44, H 3.62, N 8.73 SIMS (MH$^+$): 321

Reference Example 37

In the same manner as in Reference Example 24, 1-(1R, 2S)-2-(2,4-difluorophenyl)-2,3-epoxy-1-methylpropyl]-4-[4(2,2,3,3-tetrafluoropropoxy)phenyl]-2,3-piperazinedione was obtained.

Colorless powdery crystals.

$^1$H-NMR (CDCl$_3$) δ: 1.26 (3H,d,J=7 Hz), 2.81 (1H,d,J=5 Hz), 3.13 (1H,d,J=5 Hz), 3.61–3.81 (3H,m), 3.90–4.04 (1H, m), 4.36 (2H,t,J=12 Hz), 5.40 (1H,q,J=7 Hz), 6.06 (1H,tt, J=53 Hz,5 Hz), 6.80–6.95 (2H,m), 6.97 (2H,d,J=9 Hz), 7.32 (2H,d,J=9 Hz), 7.35–7.47 (1H,m).

Elemental analysis for $C_{23}H_{20}F_6N_2O_4$ Calcd (%): C 54.99, H 4.01, N 5.58 Found (%): C 54.61, H 4.01, N 5.65 mp 197°–201° C.

Reference Example 38

In the same manner as in Reference Example 36, starting from 4-(1,1,2,2-tetrafluoroethoxy)aniline, 1-[4-(1,1,2,2-tetrafluoroethoxy)phenyl]-2,3-piperazinedione was obtained.

Colorless powdery crystals.

$^1$H-NMR (DMSO-d$_6$) δ: 3.46–3.53 (2H,m), 3.90–3.96 (2H,m), 6.81 (1H,tt,J=52 Hz,3 Hz), 7.33 (2H,d,J=9 Hz), 7.50 (2H,d,J=9 Hz), 8.78 (1H,br).

Elemental analysis for $C_{12}H_{10}F_4N_2O_3$ Calcd (%): C 47.07, H 3.29, N 9.15 Found (%): C 46.86, H 3.24, N 9.11 mp 240°–242° C.

Reference Example 39

In the same manner as in Reference Example 24, 1-[(1R, 2S)-2-(2,4-difluorophenyl)-2,3-epoxy-1-methylpropyl]-4-[4-(1,1,2,2-tetrafluoroethoxy)phenyl]-2,3-piperazinedione was obtained.

Colorless powdery crystals.

$^1$H-NMR (CDCl$_3$) δ: 1.25 (3H,d,J=7 Hz), 2.80 (1H,d,J=5 Hz), 3.13 (tH,d,J=5 Hz), 3.60–3.85 (3H,m), 3.95–4.08 (1H, m), 5.37 (1H,q,J=7 Hz), 5.92 (1H,tt,J=53 Hz,3 Hz), 6.81–6.93 (2H,m), 7.25 (2H,d,J=8 Hz), 7.34–7.45 (3H,m).

mp 214°–215° C.

Elemental analysis for $C_{22}H_{18}F_6N_2O_4$ Calcd (%): C 54.11, H 3.71, N 5.74 Found (%): C 53.88, H 3.68, N 5.72

Reference Example 40

In the same manner as in Reference Example 1, starting from 2-(2-fluorophenyl)-2-[(1R)-1-(3,4,5,6-tetrahydro-2H-pyran-2-yl)oxyethyl]oxirane (synthesized by the method described in EP 0548553A), [(1R)-1-[(2R)-2-(2-fluorophenyl)-2-oxiranyl]ethyl]3,5-dinitrobenzoate was obtained.

Colorless prisms (recrystallized from ethyl acetate) mp 183°–184° C.

$^1$H-NMR (CDCl$_3$) δ: 1.47 (3H,dd,J=6.6 Hz,1.6 Hz), 3.03 (1H,d,J=4.7 Hz), 3.23 (1H, d, J=4.7 Hz), 5.35 (1H, q, J=6.6 Hz), 7.09–7.59 (4H,m), 9.13 (2H,t,J=2.2 Hz), 9.23 (1H,t,J= 2.2 Hz).

$[α]_D^{23}$ −24.7° C. (C=1.0, CHCl$_3$)

Elemental analysis for $C_{17}H_{13}FN_2O_7$ Calcd (%): C 54.26, H 3.48, N 7.44 Found (%): C 54.23, H 3.25, N 7.41

Reference Example 41

In the same manner as in Reference Example 3, starting from [(1R)-1-[(2R)-2-(2-fluorophenyl)-2-oxiranyl]ethyl]3, 5-dinitrobenzoate, (1R)-1-[(2R)-2-(2-fluorophenyl)-2-oxiranyl]ethanol was obtained.

Colorless oily substance.

$^1$H-NMR (CDCl$_3$) δ: 1.17 (3H,dd,J=6.6 Hz,1.0 Hz), 1.78 (1H,d,J=8.2 Hz), 2.81 (1H,d,J=5.3 Hz), 3.32 (1H,d,J=5.3 Hz), 4.15 (1H,m), 6.99–7.47 (4H,m).

Reference Example 42

In the same manner as in Reference Example 4, starting from (1R)-1-[(2R)-2-(2-fluorophenyl)-2-oxiranyl]ethanol, (1S)-1-[(2R)-2-(2-fluorophenyl)-2-oxiranyl]ethanol was obtained.

Colorless oily substance.

$^1$H-NMR (CDCl$_3$) δ: 1.21 (3H,d,J=7 Hz), 2.27 (1H,d,J=2 Hz), 2.96 (1H,d,J=5 Hz), 3.30 (1H,d,J=5 Hz), 4.16 (1H,dd, J=7 Hz, 2 Hz), 7.03–7.44 (4H,m).

Reference Example 43

In the same manner as in Reference Example 24, 1-[(1R, 2S)-2,3-epoxy-2-(2-fluorophenyl)-1-methylpropyl]-3-[4-(1,1,2,2 -tetrafluoroethoxy)phenyl]-2-imidazolidinone was obtained.

Colorless powdery crystals (recrystallized from diisopropyl ether)

mp 148°–149° C.

$^1$H-NMR (CDCl$_3$) δ: 1.24 (3H,d,J=7.2 Hz), 2.78 (1H,d, J=5.0 Hz), 3.15 (1H,d,J=5.0 Hz), 3.45–3.84 (4H,m), 4.85 (1H,q,J=7.2 Hz), 5.90 (1H,tt,J=53.2 Hz,2.8 Hz), 7.02–7.60 (8H,m).

Elemental analysis for $C_{21}H_{19}F_5N_2O_3$ Calcd (%): C 57.02, H 4.33, N 6.33 Found (%): C 56.90, H 4.36, N 6.31

Reference Example 44

In the same manner as in Reference Example 24, 1-[(1R, 2S)-2,3-epoxy-2-(2-fluorophenyl)-1-methylpropyl]-3-[4-(2, 2,3,3-tetrafluoropropoxy)phenyl]-2-imidazolidinone was obtained.

Colorless powdery crystals (recrystallized from diisopropyl ether)

mp 144°–145° C.

¹H-NMR (CDCl₃) δ: 1.22 (3H,d,J=7.4 Hz), 2.77 (1H,d, J=5.0 Hz), 3.16 (1H,d,J=5.0 Hz), 3.47–3.77 (4H,m), 4.32 (2H,tt,J=12 Hz,1.6 Hz), 4.85 (1H,q,J=7.4 Hz), 6.07 (1H,tt, J=53 Hz,5 Hz), 6,89–7.52 (8H,m).

Elemental analysis for $C_{22}H_{21}F_5N_2O_3$ Calcd (%): C 57.90, H 4.64, N 6.14 Found (%): C 57.94, H 4.60, N 6.19

Reference Example 45

(2R,3S)-2-(4-Fluorophenyl)-3-methyl-2-(1H-1,2,4-triazol-1-yl)methyloxirane (1.5 g), 2.66 g of 1-[4-(1,1,2,2-tetrafluoroethoxy)phenyl]-2(1H,3H)-imidazolone and 6.3 g of cesium carbonate were added to 25 ml of N,N-dimethylformamide. The mixture was stirred at 80° C. for five hours. After cooling, the reaction solution was diluted with 100 ml of ethyl acetate, and washed with water (100 ml×2) and a saturated aqueous solution of sodium chloride (100 ml) successively. The ethyl acetate layer was dried over anhydrous magnesium sulfate and the solvent was distilled off under reduced pressure. The residue was purified by silica gel chromatography (eluent: hexane/ethyl acetate=2/3) to give 1.21 g of 1-[(1R,2R)-2-(4-fluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone as colorless powdery crystals.

¹H-NMR (CDCl₃) δ: 1.20 (3H,d,J=7.2 Hz), 4.19 (1H,d, J=14 Hz), 4.70 (1H,d,J=14 Hz), 4.79 (1H,q,J=7.2 Hz), 5.34–5.39 (1H,bs), 5.92 (1H,tt,J=2.5Hz,53 Hz), 6.63 (1H,d, J=3 Hz), 6.78 (1H,d,J=3 Hz), 6.94-7.03 (2H,m), 7.28–7.39 (4H,m), 7.66 (2H,d,J=9 Hz), 7.69 (1H,s), 7.78 (1H,s).

Reference Example 46

In the same manner as in Reference Example 45, 1-[(1R, 2R)-2-(4-fluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone was obtained.

¹H-NMR (CDCl₃) δ: 1.20 (3H,d,J=7 Hz), 4.20 (1H,d,J= 14 Hz), 4.41 (2H,t,J=12 Hz), 4.68–4.80 (2H,m), 5.42–5.48 (1H,bs), 6.07 (1H,tt,J=5 Hz,53 Hz), 6.59 (1H,d,J=3 Hz), 6.76 (1H,d,J=3 Hz), 6.92–7.04 (2H,m), 7.30-7.39 (4H,m), 7.58 (2H,d,J=9 Hz), 7.66 (1H,s), 7.78 (1H,s).

Reference Example 47

In the same manner as in Reference Example 45, 1-[(1R, 2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone was obtained.

¹H-NMR (CDCl₃) δ: 1.20 (3H,d,J=7 Hz), 4.19 (1H,d,J= 14 Hz), 4.97 (1H,q,J=7 Hz), 5.10 (1H,d,J=14 Hz), 5.41–5.59 (1H,br), 5.93 (1H,tt,J=53 Hz,2.8 Hz), 6.64 (1H,d,J=3 Hz), 6.77 (1H,d,J=3 Hz), 6.74–6.87 (2H,m), 7.30 (2H,d,J=9 Hz 7.40–7.56 (1H,m), 7.66 (2H,d,9 Hz), 7.74 (1H,s), 7.85 (1H,s).

Reference Example 48

In the same manner as in Reference Example 45, 1-[(1R, 2R)-2-(2,4-difluorophenyl)-2-hydroxy-1-methyl-3-(1H-1,2, 4-triazol-1-yl)propyl]-3-[4-(2,2,3,3-tetrafluoropropoxy)phenyl]-2(1H,3H) -imidazolone was obtained.

¹H-NMR (CDCl₃) δ: 1.20 (3H,d,J=7 Hz), 4.20 (1H,d,J= 14 Hz), 4.37 (2H,t,J=12 Hz), 4.94 (1H,q,J=7 Hz), 5.09 (1H,d,J=14 Hz), 5.54–5.75 (1H,br), 6.06 (1H,tt,J=53 Hz,5 Hz), 6.59 (1H,d,J=3 Hz), 6.72 (1H,d,J=3 Hz), 6.74–6.86 (2H,m), 7.00 (2H,d,J=9 Hz), 7.42–7.55 (1H,m), 7.57 (2H, d,9 Hz), 7.72 (1H,s), 7.85 (1H,s).

Reference Example 49

(2R,3S)-2-(2-Fluorophenyl)-3-methyl-2-(1H-1,2,4-triazol-1-yl)methyloxirane (1.5 g), 2.66 g of 1-[4-(1,1,2,2-tetrafluoroethoxy)phenyl]-2(1H,3H)-imidazolone and 0.386 g of 60% sodium hydride in oil were added to 25 ml of N,N-dimethylformamide. The mixture was stirred at 80° C. for 20 hours. After cooling, the reaction mixture was added to 100 ml of water and extracted with ethyl acetate (50 ml×2). The extract was washed with water, dried over anhydrous magnesium sulfate and then distilled off under reduced pressure. The residue was purified by silica gel column chromatography (eluent: hexane/ethyl acetate=3/2) to give 0.27 g of 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone as a colorless powder.

Elemental analysis for $C_{23}H_{20}F_5N_5O_3$ Calcd (%): C 54.23, H 3.96, N 13.75 Found (%): C 53.83, H 3.99, N 13.56

¹H-NMR (CDCl₃) δ: 1.20 (3H,d,J=7 Hz), 4.20 (1H,d,J= 14 Hz), 5.05 (1H,q,J=7 Hz), 5.16 (1H,d,J=14 Hz), 5.30–5.41 (1H,br), 5.93 (1H,tt,J=53 Hz,2.8 Hz), 6.65 (1H,d,J=3 Hz), 6.81 (1H,d,J=3 Hz), 6.98–7.08 (2H,m), 7.18–7.51 (2H,m), 7.30 (2H,d,J=9 Hz), 7.70 (2H,d,J=9 Hz), 7.73 (1H,s), 7.81 (1H,s).

Reference Example 50

In the same manner as in Reference Example 20, starting from (1S)-1-[(2R)-2-(2-fluorophenyl)-2-oxiranyl]ethanol, the following compounds were obtained.

1-[(1R,2S)-2-(2-fluorophenyl)-2,3-epoxy-1-methylpropyl]-3-[4-(2,2,3,3-tetrafluoropropoxy)phenyl]-2(1H,3H)-imidazolone:

Colorless powdery crystals (recrystallized from diisopropyl ether)

mp 118°–119° C.

¹H-NMR (CDCl₃) δ: 1.37 (3H,d,J=7 Hz), 2.72 (1H,d,J=5 Hz), 2.81 (1H,d,J=5 Hz), 4.36 (2H,tt,J=12 Hz,2 Hz), 5.12 (1H,q,J=7 Hz), 6.07 (1H,tt,J=53 Hz,5 Hz), 6.45(1H,d,J=3 Hz), 6.51 (1H,d,J=3 Hz), 6.98 (2H,d,J=9 Hz), 7.04–7.19 (2H,m), 7.28–7.47 (2H,m), 7.57 (2H,d,J=9 Hz).

1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone:

Colorless powdery crystals

Elemental analysis for $C_{24}H_{22}F_5N_5O_3$ Calcd (%): C 55.07, H 4.24, N 13.38 Found (%): C 54.98, H 4.18, N 13.35

¹H-NMR (CDCl₃) δ: 1.20 (3H,d,J=7 Hz), 4.21 (1H,d,J= 14 Hz), 4.37 (2H,t,J=12 Hz), 4.95–5.11 (1H,m), 5.15 (1H, d,J=14 Hz), 5.34–5.56 (1H,br), 6.07 (1H, tt, J=53 Hz, 5 Hz), 6.59 (1H,d,J=3 Hz), 6.76 (1H,d,J=3 Hz), 6.97–7.07 (2H,m), 7.01 (2H,d,J=9 Hz), 7.17–7.29 (1H,m), 7.44–7.52 (1H,m), 7.59 (2H,d,J=9 Hz), 7.72 (1H,s), 7.82 (1H,s).

Reference Example 51

In the same manner as in Reference Example 1, starting from 2-(2-fluorophenyl)-2-[(1R)-1-(3,4,5,6-tetrahydro-2H-pyran-2-yl)oxyethyl]oxirane (synthesized by the method described in EP 0548553A), (1R)-1-[2-(2-fluorophenyl)-2-oxiranyl]ethanol was obtained. To a solution of this product (34.77 g) in tetrahydrofuran (600 ml) were added, with ice cooling, 127.21 g of triphenyl phosphine, 102.88 g of 3,5-dinitrobenzoic acid and 84.47 g of diethyl azodicarboxylate, and the resulting mixture was stirred at room temperature for 7 hours under an atmosphere of argon. To the reaction solution were added 600 ml of ethyl acetate, 100 ml of diisopropyl ether and 800 ml of water to fractionate and the aqueous layer was extracted with ethyl acetate (600 ml, 400 ml). The organic layers were combined, washed with water and a saturated aqueous solution of sodium chloride successively, then dried over anhydrous magnesium sulfate and concentrated. The residue was purified by silica gel column chromatography (eluent: hexane/ethyl acetate=5/1) to give 23.15 g of [(1S)-1-[(2R)-2-(2-fluorophenyl)-2-oxiranyl)ethyl]3,5-dinitrobenzoate as colorless needles.

$^1$H-NMR (CDCl$_3$) δ: 1.47 (3H,d,J=7 Hz), 2.97 (1H,d,J=5 Hz), 3.29 (1H,d,J=5 Hz), 5.43 (1H,q,J=7 Hz), 7.02–7.56 (4H,m), 9.06 (2H,d,J=2 Hz), 9.21 (1H,t,J=2 Hz).

This product (22.91 g) was dissolved in 700 ml of methanol and, with ice cooling, 146.5 ml of 1N sodium hydroxide was added thereto. The reaction solution was stirred at room temperature for one hour. To the reaction solution was added 85.5 ml of 1N hydrochloric acid and the solvent was distilled off under reduced pressure. Ethyl acetate (500 ml) and water (500 ml) were added to the residue to fractionate. The organic layer was washed with water and a saturated aqueous solution of sodium chloride successively, then dried over anhydrous magnesium sulfate and concentrated. The residue was purified by silica gel column chromatography (eluent: hexane/ethyl acetate=3/1) to give 10.76 g of (1S)-1-[(2R)-2-(2-fluorophenyl)-2-oxiranyl]ethanol as a colorless oily substance. This product was identical with the compound obtained in Reference Example 42.

Reference Example 52

60% Sodium hydride in oil (2.4 g) was added portionwise to a stirred solution of 1-[4-(1,1,2,2-tetrafluoroethoxy)phenyl]-2(1H,3H)-imidazolone (16.6 g) and the resulting mixture was stirred for 30 minutes at room temperature. (2R, 3S)-2-(2,4-Difluorophenyl)-3-methyl-2-(1H-1,2,4-triazol-1-yl)methyloxirane (10 g) was added and the mixture was stirred at 80° C. for 20 hours. After cooling, the mixture was concentrated into a volume of about 50 ml under reduced pressure and diluted ice-water (400 ml) and ethyl acetate (500 ml). The ethyl acetate layer was separated, washed with a 10% aqueous phosphoric acid solution (400 ml) and an aqueous solution of sodium chloride (400 ml×2) successively and dried over anhydrous magnesium sulfate. The solvent was distilled off under reduced pressure and the residue was purified by silica gel column chromatography (eluent: hexane/ethyl acetate=1/1 to 2/1) to give 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone (7.56 g) as an oily substance, which was identical with the compound obtained in the Reference Example 47.

Working Example 1

1-[(1R,2R)-2-(2,4-Difluorophenyl)-2-hydroxy-1-methyl-3-(1H-1,2,4-triazol-1-yl)propyl]-3-(4-trifluoromethoxyphenyl)-2(1H,3H)-imidazolone (100 mg) obtained in Reference Example 22 was dissolved in 10 ml of acetic acid, 50 mg of 10% palladium-carbon was added thereto and the mixture was stirred under an atmosphere of hydrogen at room temperature for eight hours. The catalyst was filtered off and the filtrate was concentrated. The residue was purified by silica gel column chromatography (eluent: hexane/ethyl acetate=1/5) to give 66 mg of 1-[(1R,2R)-2-(2,4-difluorophenyl)-2-hydroxy-1-methyl-3-(1H-1,2,4-triazol-1-yl)propyl]-3-(4-trifluoromethoxyphenyl)-2-imidazolidinone (Compound 1) 4.53 (1H,d,J=14.2 Hz), 4.60–4.80 (1H,m), 5.10 (1H,d,J=14.2 Hz), 5.40 (1H,br), 6.68–6.85 (2H,m) 7.31 (2H, d,J=9 Hz), 7.32–7.48 (1H,m), 7.69 (2H,d,J=9 Hz), 7.76 (1H,s), 7.88 (1H,s).

Working Example 2

In the same manner as in Working Example 1, starting from 1-[(1R,2R)-2-(2,4-difluorophenyl)-2-hydroxy-1-methyl-3-(1H-1,2,4-triazol-1-yl)propyl]-3-(2,4-difluorophenyl)-2(1H,3H)-imidazolone, 1-[(1R,2R)-2-(2,4-difluorophenyl)-2-hydroxy-1-methyl-3-(1H-1,2,4-triazol-1-yl)propyl]-3-(2,4-difluorophenyl)-2-imidazolidinone (Compound 2) was obtained.

Colorless powder.

$^1$H-NMR (CDCl$_3$) δ: 1.07 (3H,d,J=7 Hz), 3.65–4.05 (4H, m), 4.55 (1H,d,J=14.2 Hz), 4.45–4.65 (1H,m), 5.10 (1H,d, J=14.2 Hz), 5.60 (1H,br), 6.68–7.02 (4H,m), 7.36–7.68 (2H,m), 7.76 (1H,s), 7.93 (1H,s).

Working Example 3

A mixture of 0.41 g of 1H-1,2,4-triazole, 0.19 g of 60% sodium hydride in oil and 12 ml of dimethylformamide was stirred at room temperature for 20 minutes, 0.85 g of 1-[(1R,2S)-2-(2,4-difluorophenyl)-2,3-epoxy-1-methylpropyl]-3-(2,4-difluorophenyl)-2,4-imidazolidinedione obtained in Reference Example 24 was added thereto and the mixture was heated at 60° C. for four hours. After cooling, 20 ml of water was added to the reaction solution and the mixture was extracted with 80 ml of ethyl acetate. The extract was washed with 20 ml of a saturated aqueous solution of sodium chloride, dried over anhydrous magnesium sulfate and concentrated under reduced pressure. The residue was purified by silica gel chromatography (eluent: hexane/ethyl acetate=1/2 to 1/5) to give 0.12 g of 1-[(1R,2R)-2-(2,4-difluorophenyl)-2-hydroxy-1-methyl-3-(1H-1,2,4-triazol-1-yl)propyl]-3-(2,4-difluorophenyl)-2,4-imidazolidinedione (Compound 3) as a colorless powder.

$^1$H-NMR (CDCl$_3$) δ: 1.10 (3H,d,J=7 Hz), 4.25 (1H,d,J= 18 Hz), 4.41 (1H,d,J=14.2 Hz), 4.67 (1H,d,J=18 Hz), 4.94 (1H, dq,J=1.6 Hz,J=7 Hz), 5.15 (1H,d,J=14.2 Hz), 5.35 (1H,d,J=1.6 Hz), 6.70–6.84 (2H,m), 6.94–7.06 (2H,m), 7.27–7.44 (2H,m), 7.80 (1H,s), 7.82 (1H,s).

Working Example 4

(Method A)

In the same manner as in Working Example 1, starting from 1-[(1R,2R)-2-(2,4-difluorophenyl)-2-hydroxy-1-methyl-3-(1H-1,2,4-triazol-1-yl)propyl-3-(4-trifluoromethylphenyl)-2(1H,3H)-imidazolone, 1-[(1R,2R)-2-(2,4-difluorophenyl)-2-hydroxy-1-methyl-3-(1H-1,2,4-triazol-1-yl)propyl]-3-(4-trifluoromethylphenyl)-2-imidazolidinone (Compound 4) was obtained.

(Method B)

The same reaction as in Working Example 3 was carried out using 1-[(1R,2S)-2-(2,4-difluorophenyl)-2,3-epoxy-1-methylpropyl]-3-(4-trifluoromethylphenyl)-2-imidazolidinone obtained in Reference Example 33 to give 1-[(1R,2R)-2-(2,4-difluorophenyl)-2-hydroxy-1-methyl-3-(1H-1,2,4- triazol-1-yl)propyl]-3-(4-trifluoromethylphenyl)-2-imidazolidinone (Compound 4) as a colorless powder.

Elemental analysis for $C_{22}H_{20}F_5N_5O_2$ Calcd (%): C 54.89, H 4.19, N 14.55 Found (%): C 54.72, N 4.19, N 14.29

$^1$H-NMR (CDCl$_3$) δ: 1.07 (3H,d,J=7 Hz), 3.60–4.12 (4H, m), 4.49 (1H,d,J=14.2 Hz), 4.60–4.80 (1H,m), 5.11 (1H,d, J=14.2 Hz), 5.36 (1H,br), 6.70–6.85 (2H,m), 7.32–7.48 (1H,m), 7.60 (2H,d,J=8.8 Hz), 7.70 (1H,d,J=8.8 Hz), 7.76 (1H,s), 7.85 (1H,s).

Working Example 5

In the same manner as in Working Example 1, starting from 1-[(1R,2R)-2-(2,4-difluorophenyl)-2-hydroxy-1-methyl-3-(1H-1,2,4-triazol-1-yl)propyl]-3-(4-fluorophenyl)-2(1H,3H)-imidazolone, 1-[(1R,2R)-2-(2,4-difluorophenyl)-2-hydroxy-1-methyl-3-(1H-1,2,4-triazol-1-yl)propyl]-3-(4-fluorophenyl)-2-imidazolidinone (Compound 5) was obtained.

Colorless powdery crystals.

mp 74°–78° C. (ethyl acetate-hexane)

$^1$H-NMR (CDCl$_3$) δ: 1.06 (3H,d,J=7.0 Hz), 3.65–3.73 (1H, m), 3.79–4.00 (3H,m), 4.51 (1H,d,J=14 Hz), 4.60 (1H,m), 5.07 (1H,d,J=14 Hz), 5.3–5.7 (1H,br), 6.71–6.82 (2H,m), 6.99–7.11 (2H,m), 7.36–7.56 (3H,m), 7.74 (1H,s), 7.87 (1H,s).

IR (KBr) νmax: 3420, 1690, 1615, 1510, 1480, 1420 (cm$^{-1}$)

Working Example 6

(Method A)

In the same manner as in Working Example 1, starting from 1-[(1R,2R)-2-(2,4-difluorophenyl)-2-hydroxy-1-methyl-3-(1H-1,2,4-triazol-1-yl)propyl-3-[4-(2,2,3,3-tetrafluoropropoxy)phenyl]-2(1H,3H)-imidazolone, 1-[(1R,2R)-2-(2,4-difluorophenyl)-2-hydroxy-1-methyl-3-(1H-1,2,4-triazol-1-yl)propyl]-3-[4-(2,2,3,3-tetrafluoropropoxy)phenyl]-2-imidazolidinone (Compound 6) was obtained.

(Method B)

In the same manner as in Working Example 3, starting from 1-[(1R,2S)-2-(2,4-difluorophenyl)-2,3-epoxy-1-methylpropyl]-3-[4-(2,2,3,3-tetrafluoropropoxy)phenyl]-2-imidazolidinone, 1-[(1R,2R)-2-(2,4-difluorophenyl)-2-hydroxy-1-methyl-3-(1H-1,2,4-triazol-1-yl)propyl]-3-[4-(2,2,3,3-tetrafluoropropoxy)phenyl]-2-imidazolidinone (Compound 6) was obtained.

Colorless powdery crystals.

$^1$H-NMR (CDCl$_3$) δ: 1.06 (3H,d,J=7.0 Hz), 3.66–3.73 (1H, m), 3.80–3.95 (3H,m), 4.33 (2H,tt,J=12 Hz,1.6 Hz), 4.52 (1H, d,J=14.4 Hz), 4.5–4.65 (1H,m), 5.08 (1H,d,J=14.4 Hz), 5.45–5.65 (1H,br), 6.06 (1H,tt,J=53 Hz,4.8 Hz), 6.70–6.83 (2H,m), 6.94 (2H,d,J=9.2 Hz), 7.39–7.54 (1H,m), 7.50 (2H,d,J=9.2 Hz), 7.74 (1H,s), 7.88 (1H,s).

Elemental analysis for $C_{24}H_{23}F_6N_5O_3$ Calcd (%): C 53.04, H 4.27, N 12.89 Found (%): C 53.04, H 4.50, N 12.82

IR (KBr) νmax: 3380, 1690, 1665, 1510, 1485, 1440 (cm$^{-1}$).

Working Example 7

(Method A)

In the same manner as in Working Example 1, starting from 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone, 1-[(1R,2R)-2-(2, 4-difluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (Compound 7) was obtained.

(Method B)

In the same manner as in Working Example 3, starting from 1-[(1R,2S)-2-(2,4-difluorophenyl)-2,3-epoxy-1-methylpropyl]-3-[4-(1,1,2,2-tetrafluoroethoxy)phenyl]-2-imidazolidinone, 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (Compound 7) was obtained.

Colorless powdery crystals.

$^1$H-NMR (CDCl$_3$) δ: 1.07 (3H,d,J=7 Hz), 3.67–3.75 (1H, m), 3.82–4.01 (3H,m), 4.50 (1H,d,J=15 Hz), 4.65 (1H,m), 5.10 (1H, d,J=15 Hz), 5.3–5.6 (1H,br), 5.91 (1H,tt,J=53 Hz,3.0 Hz), 6.72–6.83 (2H,m), 7.21 (2H,d,J=9.2 Hz), 7.36–7.49 (1H,m), 7.58 (2H,d,J=9.2 Hz), 7.75 (1H,s), 7.86 (1H,s).

Elemental analysis for $C_{23}H_{21}F_6N_5O_3$ Calcd (%): C 52.18, N 4.00, N 13.23 Found (%): C 52.30, H 3.95, N 13.28

IR (KBr) νmax: 3380, 1680, 1615, 1510, 1480, 1425 (cm$^{-1}$).

Working Example 8–14

In the same manner as in Working Example 3, the following compounds were obtained.

Working Example 8

Starting from 1-[(1R,2S)-2-(2,4-difluorophenyl)-2,3-epoxy-1-methylpropyl]-3-[4-(2,2,3,3,3-pentafluoropropoxy)phenyl]-2-imidazolidinone, 1-[(1R,2R)-2-(2,4-difluorophenyl)-2-hydroxy-1-methyl-3-(1H-1,2,4-triazol-1-yl)propyl]-3-[4-(2,2,3,3,3-pentafluoropropoxy)phenyl]-2-imidazolidinone (Compound 8) was obtained.

Colorless powder.

$^1$H-NMR (CDCl$_3$) δ: 1.06 (3H,d,J=7.2 Hz), 3.66–3.73 (1H, m), 3.79–4.01 (3H,m), 4.41 (2H,t,J=12.4 Hz), 4.52 (1H,d,J=14 Hz), 4.51–4.68 (1H,m), 5.08 (1H,d,J=14 Hz), 5.3–5.8 (1H,br), 6.71–6.82 (2H,m), 6.96 (2H,d,J=9.2 Hz), 7.37–7.5 (1H,m), 7.51 (2H,d,J=9.2 Hz), 7.74 (1H,s), 7.88 (1H,s).

Elemental analysis for $C_{24}H_{22}F_7N_5O_3$ Calcd (%): C 51.34, H 3.95, N 12.47 Found (%): C 51.14, H 3.95, N 12.32

IR (KBr) νmax: 3420, 1690, 1610, 1510, 1480, 1425 (cm$^{-1}$).

Working Example 9

Starting from 1-[(1R,2S)-2-(2,4-difluorophenyl)-2,3-epoxy-1-methylpropyl]-3-[4-(2,2,2-trifluoroethoxy)phenyl]-2-imidazolidinone, 1-[(1R,2R)-2-(2,4-difluorophenyl)-2-hydroxy-1-methyl-3-(1H-1,2,4-triazol-1-yl)propyl]-3-[4-(2,2,2-trifluoroethoxy)phenyl]-2-imidazolidinone (Compound 9) was obtained.

Colorless powdery crystals.

mp 80°–83° C. (diethyl ether)

$^1$H-NMR (CDCl$_3$) δ: 1.06 (3H,d,J=7.2 Hz), 3.65–3.74 (1H, m), 3.79–3.95 (3H,m), 4.34 (2H,q,J=8 Hz), 4.52 (1H, d,J=14 Hz), 4.5–4.65 (1H,m), 5.08 (1H,d,J=14 Hz), 5.4–5.7 (1H,br), 6.71–6.81 (2H,m), 6.96 (2H,d,J=9.2 Hz), 7.38–7.5 (1H,m), 7.50 (2H, d,J=9.2 Hz), 7.74 (1H,s), 7.88 (1H,s).

Elemental analysis for $C_{23}H_{22}F_5N_5O_3$ Calcd (%): C 54.01, H 4.34, N 13.69 Found (%): C 53.67, H 4.27, N 13.79

IR (KBr) νmax: 3410, 1690, 1610, 1510, 1480, 1420 (cm$^{-1}$).

Working Example 10

Starting from 1-(4-chlorophenyl)-3-[(1R,2S)-2-(2,4-difluorophenyl)-2,3-epoxy-1-methylpropyl]-2-imidazolidinone, 1-(4-chlorophenyl)-3-[(1R,2R)-2-(2,4-difluorophenyl)-2-hydroxy-1-methyl-3-(1H-1,2,4-triazol-1-yl)propyl]-2-imidazolidinone (Compound 10) was obtained.

Colorless powdery crystals.

mp 138°–139° C. (diethyl ether-hexane).

$^1$H-NMR (CDCl$_3$) δ: 1.06 (3H,d,J=7.0 Hz), 3.64–3.75 (1H, m), 3.80–4.03 (3H,m), 4.50 (1H,d,J=15 Hz), 4.54–4.72 (1H,m), 5.09 (1H,d,J=15 Hz), 5.3–5.6 (1H,br), 6.73–6.83 (2H,m), 7.31 (2H,d,J=9 Hz), 7.35–7.45 (1H,m), 7.52 (2H, d,J=9 Hz), 7.75 (1H, s), 7.86 (1H,s).

Elemental Analysis for C$_{21}$H$_{20}$C$_1$F$_2$N$_5$O$_2$ Calcd (%): C 56.32, H 4.50, N 15.64 Found (%): C 56.35, H 4.36, N 15.93

IR (KBr) νmax: 3400, 1695, 1660, 1618, 1500, 1420, 1270 (cm$^{-1}$).

Working Example 11

Starting from 1-[(1R,2S)-2-(2,4-difluorophenyl)-2,3-epoxy-1-methylpropyl]-4-[4-(2,2,3,3-tetrafluoropropoxy)phenyl]-2,5-piperazinedione, 1-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-2,5-piperazinedione (Compound 11) was obtained.

Colorless powder.

$^1$H-NMR (CDCl$_3$) δ: 1.07(3H,d,J=7 Hz), 4.24–4.52 (6H, m), 4.74 (1H,d,J=18 Hz), 5.16 (1H,d,J=14 Hz), 5.29 (1H,s), 5.36 (1H,q,J=7 Hz), 6.06 (1H,tt,J=53 Hz,5 Hz), 6.74–6.83 (2H,m), 7.00 (2H,d,J=9 Hz), 7.29 (2H,d,J=9 Hz), 7.31–7.47 (1H,m), 7.80 (1H,s ), 7.82 (1H,s).

IR (KBr) νmax: 3410, 1660, 1610, 1505, 1450, 1315 (cm$^{-1}$).

Working Example 12

Starting from 1-[(1R,2S)-2-(2,4-difluorophenyl-2,3-epoxy-1-methylpropyl]-4-[4-(1,1,2,2-tetrafluoroethoxy)phenyl]-2,5-piperazinedione, 1-[(1R,2R)-2-(2,4-difluorophenyl)-2-hydroxy-1-methyl-3-(1H-1,2,4-triazol-1-yl)propyl]-4-[4-(1,1,2,2-tetrafluoroethoxy)phenyl]-2,5-peperazinedione (Compound 12) was obtained.

White powder.

$^1$H-NMR (CDCl$_3$) δ: 1.07 (3H,d,J=7 Hz), 4.25–4.38 (2H, m), 4.45 (2H,s), 4.74 (1H,d,J=17 Hz), 5.15 (1H,d,J=14 Hz), 5.30–5.41 (2H,m), 5.92 (1H,tt,J=53 Hz,3 Hz), 6.73–6.82 (2H,m), 7.28 (2H,d,J=9 Hz), 7.30–7.45 (3H,m), 7.79 (1H,s), 7.82 (1H,s).

Elemental analysis for C$_{24}$H$_{21}$F$_6$N$_5$O$_4$ Calcd (%): C 51.71, H 3.80, N 12.56 Found (%): C 51.54, H 3.79, N 12.56

Working Example 13

Starting from 1-[(1R,2S)-2-(2,4-difluorophenyl-2,3-epoxy-1-methylpropyl]-4-[4-(2,2,3,3-tetrafluoropropoxy)phenyl]-2,3-piperazinedione, 1-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-2,3-piperazinedione (Compound 14) was obtained.

White powder $^1$H-NMR (CDCl$_3$) δ: 1.07 (3H,d,J=7 Hz), 3.79–3.90 (2H, m), 4.04–4.27 (2H,m), 4.36 (2H,t,J=12 Hz), 4.39 (1H,d,J=13 Hz), 5.24 (1H,d,J=13 Hz), 5.27–5.40 (2H,m), 6.06 (1H,tt, J=53 Hz,5 Hz), 6.72–6.83 (2H,m), 6.98 (2H,d,J=9 Hz), 7.31–7.44 (3H,m), 7.78 (1H,s), 7.82 (1H,s).

Elemental analysis for C$_{25}$H$_{23}$F$_6$N$_5$O$_4$ Calcd (%): C 52.54, H 4.06, N 12.25 Found (%): C 52.34, H 4.12, N 12.10

Working Example 14

Starting from 1-[(1R,2S)-2-(2,4-difluorophenyl)-2,3-epoxy-1-methylpropyl]-4-[4-(1,1,2,2-tetrafluoroethoxy)phenyl]-2,3-piperazinedione, 1-[(1R,2R)-2-(2,4-difluorophenyl)-2-hydroxy-1-methyl-3-(1H-1,2,4-triazol-1-yl)propyl]-4-[4-(1,1,2,2-tetrafluoroethoxy)phenyl]-2,3-piperazinedione (Compound 15) was obtained.

Colorless powdery crystals $^1$H-NMR (CDCl$_3$) δ: 1.07 (3H,d,J=7 Hz), 3.78–3.98 (2H, m), 4.10–4.29 (2H,m), 4.40 (1H,d,J=15 Hz), 5.25 (2H,d,J= 15 Hz), 5.25–5.40 (2H,m), 5.93 (1H, tt, J=53 Hz, 3 Hz), 6.73–6.84 (2H,m), 7.28 (2H,d,J=9 Hz), 7.30–7.42 (1H,m), 7.44 (2H,d,J=9 Hz), 7.79 (1H,s), 7.82 (1H,s).

Elemental analysis for C$_{24}$H$_{21}$F$_6$N$_5$O$_4$·0.5H$_2$O Calcd (%): C 50.89, H 3.91, N 12.36 Found (%): C 51.13, H 4.07, N 12.45 mp 174°–175° C.

Working Example 15

(Method A)

In the same manner as in Working Example 1, starting from 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone, 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (Compound 16) was obtained.

(Method B)

In the same manner as in Working Example 3, starting from 1-[(1R,2S)-2,3-epoxy-2-(2-fluorophenyl)-1-methylpropyl]-3-[4-(1,1,2,2-tetrafluoroethoxy)phenyl]-2-imidazolidinone, 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (Compound 16) was obtained.

Colorless needles.

$^1$H-NMR (CDCl$_3$) δ: 1.06 (3H,d,J=7.0 Hz), 3.68–4.05 (4H,m), 4.51 (1H,d,J=14.4 Hz), 4.65–4.80 (1H,m), 5.15 (1H,d,J=14.4 Hz), 5.25 (1H,br), 5.91 (1H,tt,J=53.2 Hz,3 Hz), 6.95–7.63 (8H,m), 7.74 (1H,s), 7.82 (1H,s).

Elemental analysis for C$_{23}$H$_{22}$F$_5$N$_5$O$_3$ Calcd (%): C 54.01, H 4.34, N 13.69 Found (%): C 53.96, H 4.48, N 13.69

Working Example 16

(Method A)

In the same manner as in Working Example 1, starting from 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone, 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone (Compound 17) was obtained.

(Method B)

In the same manner as in Working Example 3, starting from 1-[(1R,2S)-2,3-epoxy-2-(2-fluorophenyl)-1-methylpropyl]-3-[4-(2,2,3,3-tetrafluoropropoxy)phenyl]-2-imidazolidinone, 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone (Compound 17) was obtained.

Colorless powdery crystals.

$^1$H-NMR (CDCl$_3$) δ: 1.06 (3H,d,J=7.0 Hz), 3.66–4.05 (4H,m), 4.33 (2H,tt,J=12 Hz,1.6 Hz), 4.52 (1H,d,J=14 Hz), 4.60–4.77 (1H,m), 5.13 (1H,d,J=14 Hz), 5.35 (1H,br), 6.07 (1H,tt,J=53 Hz,5 Hz), 6.91–7.53 (8H,m), 7.73 (1H,s), 7.83 (1H,s).

Elemental analysis for C$_{24}$H$_{24}$F$_5$N$_5$O$_3$ Calcd (%): C 54.86, H 4.60, N 13.33 Found (%): C 54.66, H 4.57, N 13.26

Working Example 17

In the same manner as in Working Example 1, starting from 1-[(1R,2R)-2-(4-fluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone, 1-[(1R,2R)-2-(4-fluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (Compound 18) was obtained.

Colorless powdery crystals.

$^1$H-NMR (CDCl$_3$) δ: 1.06 (3H,d,J=7.2 Hz), 3.69–4.02 (4H,m), 4.42 (1H,q,J=7.2 Hz), 4.48 (1H,d,J=14 Hz), 4.72 (1H,d,J=14 Hz), 5.22–5.39 (1H,bs), 5.91 (1H,tt,J=2.4 Hz,53 Hz), 6.93–7.01 (2H,m), 7.20–7.34 (4H,m), 7.58 (2H,d,J=9 Hz), 7.65 (1H,s), 7.80 (1H,s).

Elemental analysis for C$_{23}$H$_{22}$F$_5$N$_5$O$_3$ Calcd (%): C 54.01, H 4.34, N 13.69 Found (%): C 53.82, H 4.32, N 13.66

Working Example 18

In the same manner as in Working Example 1, starting from 1-[(1R,2R)-2-(4-fluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone, 1-[(1R,2R)-2-(4-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone (Compound 19) was obtained.

Colorless powdery crystals.

$^1$H-NMR (CDCl$_3$) δ: 1.06 (3H,d,J=7.2 Hz), 3.70–3.93 (4H,m), 4.28–4.45 (3H,m), 4.49 (1H,d,J=14 Hz), 4.72 (1H,d,J=14 Hz), 5.32–5.48 (1H,bs), 6.07 (1H,tt,J=5 Hz,53 Hz), 6.93–7.00 (4H,m), 7.30–7.34 (2H,m), 7.50 (2H,d,J=9 Hz), 7.66 (1H,s), 7.80 (1H,s).

Elemental analysis for C$_{24}$H$_{24}$F$_5$N$_5$O$_3$ Calcd (%): C 54.86, H 4.60, N 13.33 Found (%): C 54.86, H 4.68, N 12.94

A preferred group of the compounds belonging to the compound (I) of the present invention is exemplified in Table 3 and in Table 4 though the present invention is not limited thereto.

TABLE 3

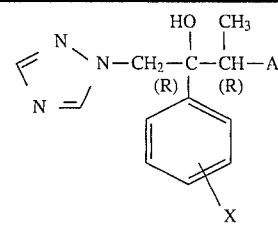

| cpd. No. | -X | -A |
|---|---|---|
| 1 | 2,4-F$_2$ | 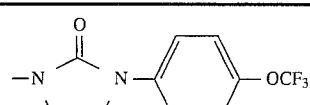 |
| 2 | 2,4-F$_2$ | 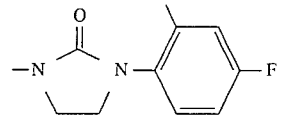 |
| 3 | 2,4-F$_2$ | 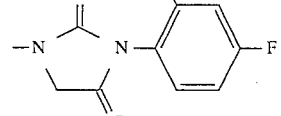 |
| 4 | 2,4-F$_2$ | 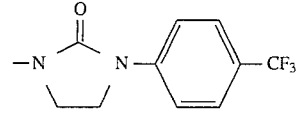 |
| 5 | 2,4-F$_2$ | 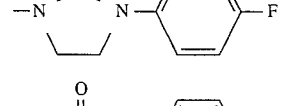 |
| 6 | 2,4-F$_2$ | 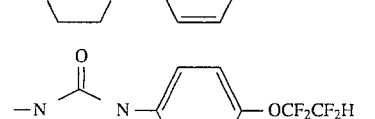 |
| 7 | 2,4-F$_2$ | 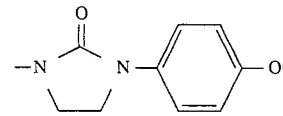 |
| 8 | 2,4-F$_2$ |  |

TABLE 3-continued $$\underset{N=}{\overset{N}{\underset{\parallel}{\bigvee}}} N-CH_2-\underset{(R)}{\overset{HO}{\underset{|}{C}}}-\underset{(R)}{\overset{CH_3}{\underset{|}{CH}}}-A$$

(with phenyl bearing X)

| cpd. No. | −X | −A |
|---|---|---|
| 9 | 2,4-F$_2$ | −N(CO-piperazinyl)-C$_6$H$_4$-OCH$_2$CF$_3$ |

TABLE 4

| cpd. No. | −X | −A |
|---|---|---|
| 10 | 2,4-F$_2$ | −N(CO-piperazinyl)-C$_6$H$_4$-Cl |
| 11 | 2,4-F$_2$ | −N(CO-piperazinedionyl)-C$_6$H$_4$-OCH$_2$CF$_2$CF$_2$H |
| 12 | 2,4-F$_2$ | −N(CO-piperazinedionyl)-C$_6$H$_4$-OCF$_2$CF$_2$H |
| 13 | 2,4-F$_2$ | −N(CO-piperazinedionyl)-C$_6$H$_4$-OCF$_3$ |
| 14 | 2,4-F$_2$ | −N(CO-piperazinedionyl)-C$_6$H$_4$-OCH$_2$CF$_2$CF$_2$H |
| 15 | 2,4-F$_2$ | −N(CO-piperazinedionyl)-C$_6$H$_4$-OCF$_2$CF$_2$H |
| 16 | 2-F | −N(CO-piperazinyl)-C$_6$H$_4$-OCF$_2$CF$_2$H |

TABLE 4-continued

| cpd. No. | −X | −A |
|---|---|---|
| 17 | 2-F | −N(CO-piperazinyl)-C$_6$H$_4$-OCH$_2$CF$_2$CF$_2$H |
| 18 | 4-F | −N(CO-piperazinyl)-C$_6$H$_4$-OCF$_2$CF$_2$H |
| 19 | 4-F | −N(CO-piperazinyl)-C$_6$H$_4$-OCH$_2$CF$_2$CF$_2$H |

Preparation 1

Using the Compound 7 obtained in Working Example 7, the components stated below were mixed. The mixture was packed in gelatin capsules to obtain capsules, each of which contains the Compound 7 in an amount of 50 mg.

| | |
|---|---|
| Compound 7 (obtained in Working Example 7) | 50 mg |
| Lactose | 100 mg |
| Cornstarch | 40 mg |
| Magnesium stearate | 10 mg |
| Total | 200 mg |

Preparation 2

The Compound 4 obtained in Working Example 4 and magnesium stearate were granulated in an aqueous solution of soluble starch. The resulting product was dried, and then mixed with lactose and cornstarch. The mixture was subjected to compression molding to obtain a tablet containing the components stated below.

| | |
|---|---|
| Compound 4 (obtained in Working Example 4) | 50 mg |
| Lactose | 65 mg |
| Cornstarch | 30 mg |
| Soluble starch | 35 mg |
| Magnesium stearate | 20 mg |
| Total | 200 mg |

Evaluation of the antifungal activities of the compound of the present invention was conducted by the following method: a sheet of filter paper disc (manufactured by Toyo Seisakusho, 8 mm in diameter) soaked in a 1000 μg/ml solution of a compound of the present invention in methanol was placed on an agar plate containing various fungi, which was incubated at 28° C. for two days, and the diameter of the growth inhibition zone around the filter paper disc was measured. The following culture media were used: A: yeast nitrogen base agar medium (pH 7.0) B: peptone-yeast extract-glucose agar medium (pH 7.0)

The antifungal spectra of the compounds of the present invention are shown in Table 5.

TABLE 5

| Test microorganism | Medium | Diameter of growth inhibition zone (mm) | | |
|---|---|---|---|---|
| | | cpd.1 | cpd.2 | cpd.4 |
| Candida albicans IFO 0583 | A | 36 | 45 | 41 |
| Candida utilis IFO 0619 | A | 25 | 29 | 31 |
| Aspergillus niger IFO 4066 | A | 24 | 27 | 26 |
| Aspergillus fumigatus IFO 6344 | A | 31 | 30 | 34 |
| Cryptococcus neoformans IFO 0410 | A | 27 | 31 | 29 |
| Trichophyton rubrum IFO 5467 | B | 47 | 50 | 43 |
| Trichophyton mentagrophytes IFO 7522 | B | 48 | 40 | 39 |
| Microsporum gypseum IFO 6076 | B | 49 | 41 | 42 |

The antifungal activities of the compound of the present invention against *Candida albicans* are shown in Table 6.

TABLE 6

| cpd. No. | Diameter of growth-inhibition zone (mm) Candida albicans IFO 0583 (Medium A. 28° C., two-day culture) |
|---|---|
| 3 | 41 |
| 5 | 47 |
| 6 | 36 |
| 7 | 35 |
| 8 | 28 |
| 9 | 41 |
| 10 | 42 |
| 11 | 31 |

The protective effects of the compound of the present invention against the experimental infection in mice are shown in the following Tables 7 and 8.

Test Method: Five-week-old Crj:CDF$_1$ mice were inoculated with the minimum lethal dose of *Candida albicans* TA intravenously. The test compound was suspended in a solution of 0.2% or 0.5% sodium carboxymethylcellulose (CMC). The suspension was administered orally once immediately after infection. The activity was expressed in terms of ED$_{50}$ values calculated by the Reed and Muench method from the survival rate 7 days after infection.

TABLE 7

| cpd. No. | ED$_{50}$ (mg/kg) P.O. [0.2% CMC] |
|---|---|
| 1 | 1.4 |
| 3 | 2.0 |
| 4 | 0.65 |
| 7 | 0.65 |
| 8 | 2.0 |
| 9 | 0.65 |
| 10 | 1.8 |

P.O. oral administration

TABLE 8

| cpd. No. | ED$_{50}$ (mg/kg) P.O. [0.5% CMC] |
|---|---|
| 6 | 0.71 |
| 7 | 0.35 |
| 12 | 2.8 |
| 14 | 2.8 |
| 15 | 2.0 |
| 16 | 0.35 |
| 17 | 0.65 |
| 18 | 0.35 |
| 19 | 0.77 |

The protective effects of the compound of formula (VI), which is a starting compound of the present invention, against the experimental infection in mice are shown in the following Table 9.

Test Method: Five-week-old Crj:CDF$_1$ mice were inoculated with the minimum lethal dose of *Candida albicans* TA intravenously. The test compound was suspended in a solution of 0.5% sodium carboxymethylcellulose (CMC). The suspension was administered orally once immediately after infection. The activity was expressed in terms of ED$_{50}$ values calculated by the Reed and Muench method from the survival rate 7 days after infection.

TABLE 9

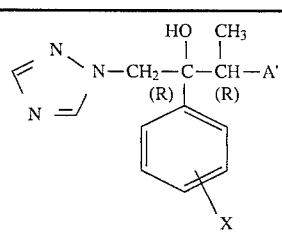

| Ref. Ex. No. | X | A' | ED$_{50}$ (mg/kg) P.O. |
|---|---|---|---|
| 45 | 4-F | | 0.18 |

TABLE 9-continued

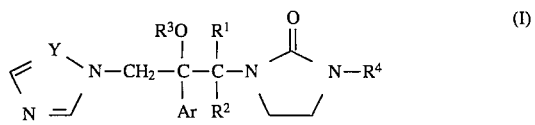

| Ref. Ex. No. | X | A' | ED$_{50}$ (mg/kg) P.O. |
|---|---|---|---|
| 46 | 4-F | —N⌒N—⟨phenyl⟩—OCH$_2$CF$_2$CF$_2$H (with C=O) | 0.32 |
| 49 | 2-F | —N⌒N—⟨phenyl⟩—OCF$_2$CF$_2$H (with C=O) | 0.18 |
| 50 | 2-F | —N⌒N—⟨phenyl⟩—OCH$_2$CF$_2$CF$_2$H (with C=O) | 0.32 |

The compound of the present invention or a salt thereof exhibits excellent antifungal activities. The compound of the present invention or a salt thereof is useful for prevention and therapy of infections of mammals as an antifungal agent. In addition, the compound of the present invention can be also used as an antifungal agent for agricultural use.

What we claimed is:

1. A compound represented by the formula (I):

$$\text{(I)}$$

wherein Ar is an optionally-substituted phenyl group; $R^1$ and $R^2$ are, the same or different, a hydrogen atom or a lower alkyl group, or $R^1$ and $R^2$ may combine together to form a lower alkylene group; $R^3$ is a hydrogen atom or an acyl group; Y is a nitrogen atom or a methine group; and $R^4$ is a substituted phenyl group, or a salt thereof.

2. A compound of claim 1 in which one of $R^1$ and $R^2$ is a hydrogen atom and another is a lower alkyl group.

3. A compound of claim 1 in which Y is a nitrogen atom.

4. A compound of claim 1 in which Ar is a halogen-substituted phenyl group.

5. A compound of claim 4 in which Ar is a phenyl group substituted with 1 or 2 fluorine atoms.

6. A compound of claim 1 in which $R^4$ is a substituted phenyl group having 1 or 2 substituents selected from the group consisting of a halogen atom, a halogenated $C_{1-6}$ alkyl group and a halogenated $C_{1-6}$ alkoxy group.

7. A compound of claim 6 in which the substituent of the substituted phenyl group is a fluorine atom, a fluorinated lower alkyl group or a fluorinated lower alkoxy group.

8. A compound of claim 1, which is 1-[(1R,2R)]-2-(2,4-difluorophenyl)-2-hydroxy-1-methyl-3-(1H-1,2,4-triazol-1-yl)propyl]-3-[4-(2,2,3,3-tetrafluoropropoxy)phenyl]-2-imidazolidinone.

9. A compound of claim 1, which is 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2-imidazolidinone.

10. A compound of claim 1, which is 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2-imidazolidinone.

11. A compound of claim 1, which is 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone.

12. A method for preventing or treating a fungal infection which comprises administering a pharmacological effective amount of a compound of the formula (I) as defined in claim 1 or its pharmaceutically acceptable salt, optionally together with a carrier or diluent, to a mammal suffering from the fungal infection.

* * * * *